United States Patent
Enamito et al.

(10) Patent No.: US 6,192,133 B1
(45) Date of Patent: Feb. 20, 2001

(54) ACTIVE NOISE CONTROL APPARATUS

(75) Inventors: Akihiko Enamito, Chigasaki; Takuro Hayashi, Yokohama, both of (JP)

(73) Assignee: Kabushiki Kaisha Toshiba, Kawasaki (JP)

(*) Notice: Under 35 U.S.C. 154(b), the term of this patent shall be extended for 0 days.

(21) Appl. No.: 08/932,176

(22) Filed: Sep. 17, 1997

(30) Foreign Application Priority Data

Sep. 17, 1996 (JP) .................................................. 8-245296

(51) Int. Cl.[7] ............................ A61F 11/06; G10K 11/16; H03B 29/00
(52) U.S. Cl. .......................................... 381/71.5; 381/71.1
(58) Field of Search .................. 381/71.1, 71.2, 381/71.3, 71.5, 71.7, 71.8, 71.11, 71.13

(56) References Cited

U.S. PATENT DOCUMENTS

| 4,153,815 | * | 5/1979 | Chaplin | 381/71.3 |
| 5,347,586 | * | 9/1994 | Hill | 381/71.8 |
| 5,515,444 | * | 5/1996 | Burdisso | 381/71.5 |
| 5,602,926 | * | 2/1997 | Ohashi | 381/71.5 |
| 5,748,750 | * | 5/1998 | L'Esperance | 381/71.5 |
| 5,822,439 | * | 10/1998 | Sakiyama | 381/71.5 |

OTHER PUBLICATIONS

Ken'iti Kido, et al., "Active Reduction of noise by additional noise source and its Limit", Journal of Vibration Acoustics, Stress, and Reliability in Design, Transactions of the ASME, vol. 111, Oct. 1989, pp. 480–485.

P.A. Nelson, et al., "The Minimum Power Output of Free Field Point Sources and the Active Control of Sound", Journal of Sound and Vibration, vol. 116, No. 3, (1987), pp. 397–414.

P.A. Nelson, et al., "The Active Minimization of Harmonic Enclosed Sound Fields, Part I: Theory", Journal of Sound and Vibration, vol. 117, No. 1, (1987), pp. 1–11.

* cited by examiner

Primary Examiner—Minsun Oh Harvey
(74) Attorney, Agent, or Firm—Oblon, Spivak, McClelland, Maier & Neustadt, P.C.

(57) ABSTRACT

A speaker, serving as an additional sound source, is provided close to a noise source, two microphones are arranged on a central axis of a vibration surface of the speaker to be spaced from each other, acoustic intensity of the speaker is measured from outputs of these microphones, and an input to the speaker is controlled by a controller such that acoustic intensity, that is, acoustic power of the speaker is set to be zero or minimized.

11 Claims, 12 Drawing Sheets

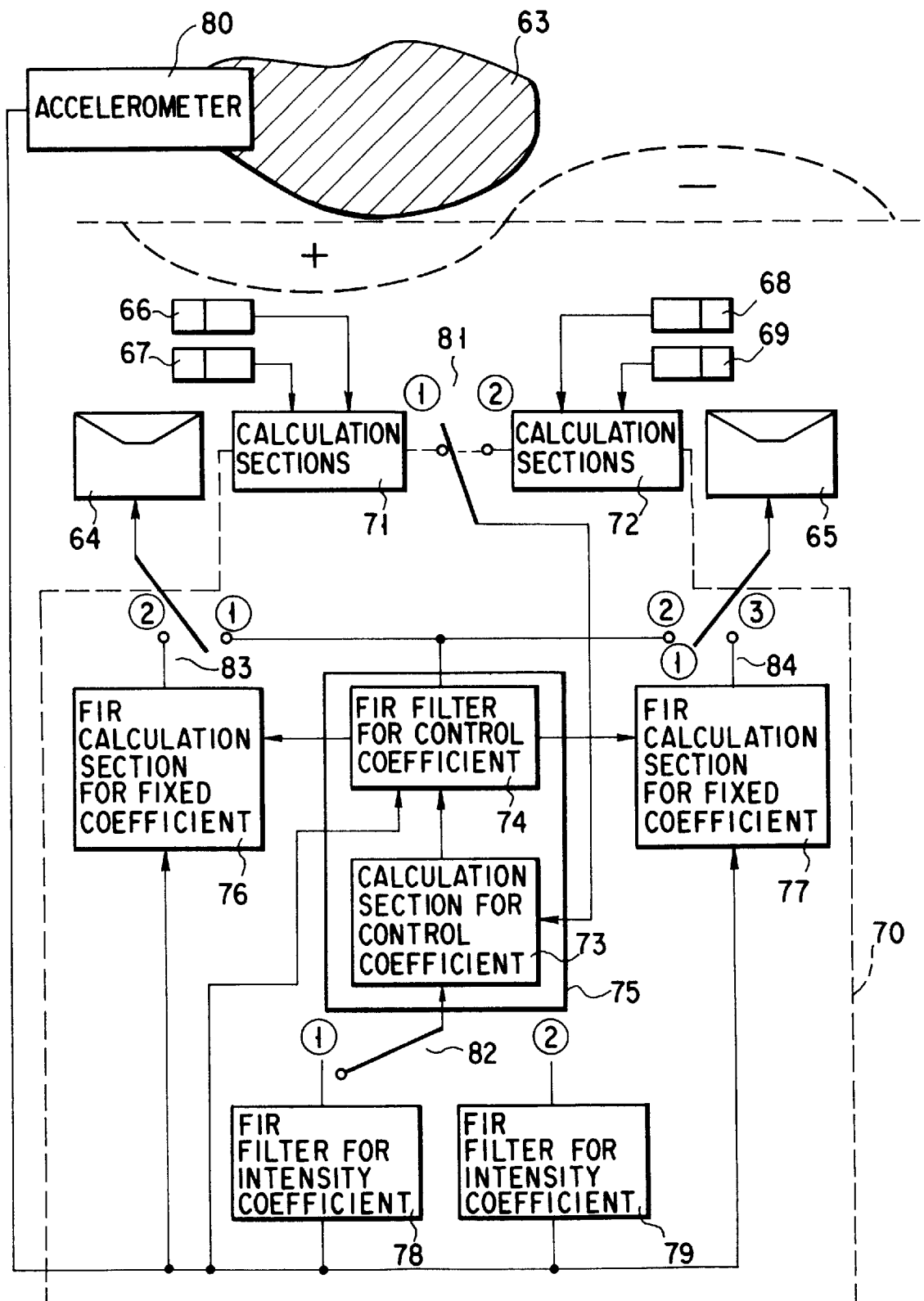
F I G. 4

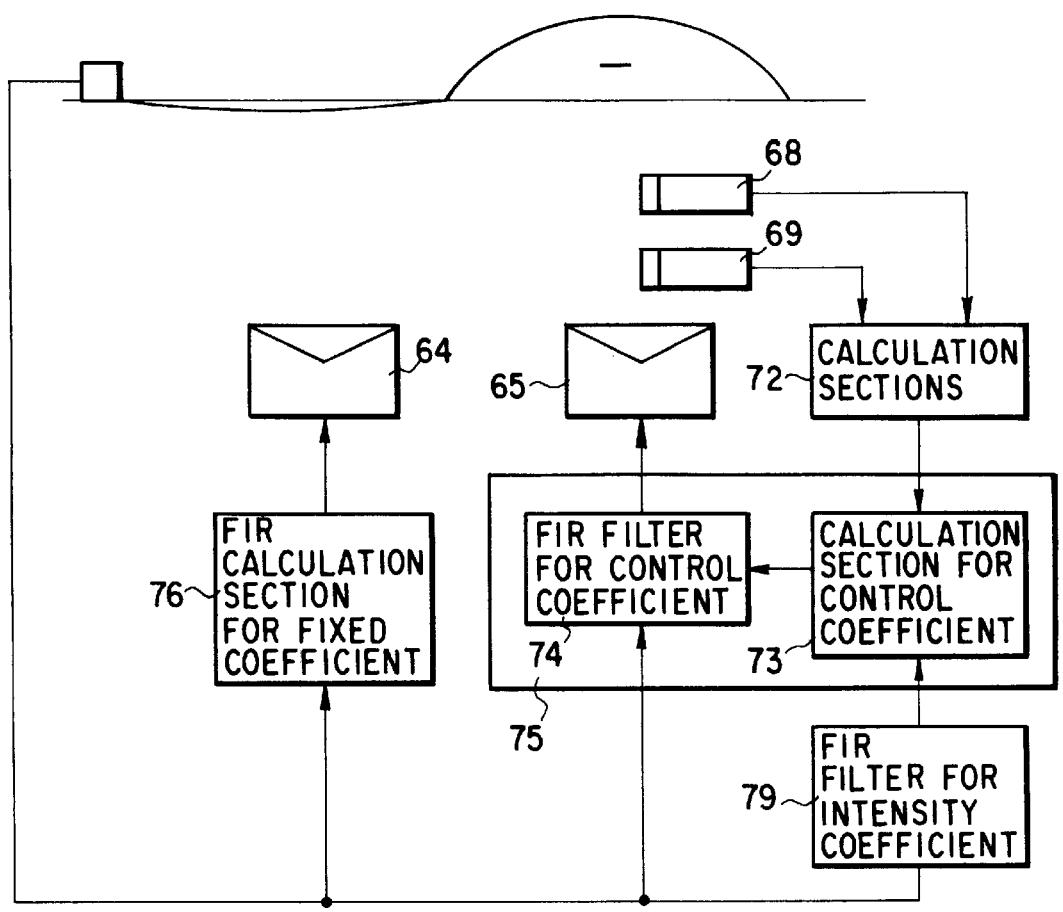
F I G. 6
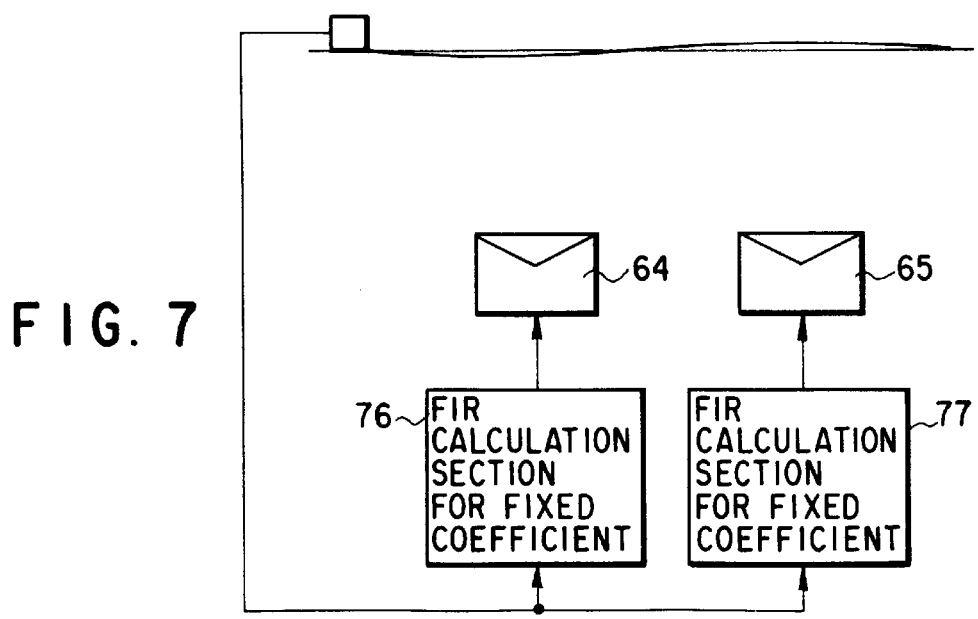
F I G. 7

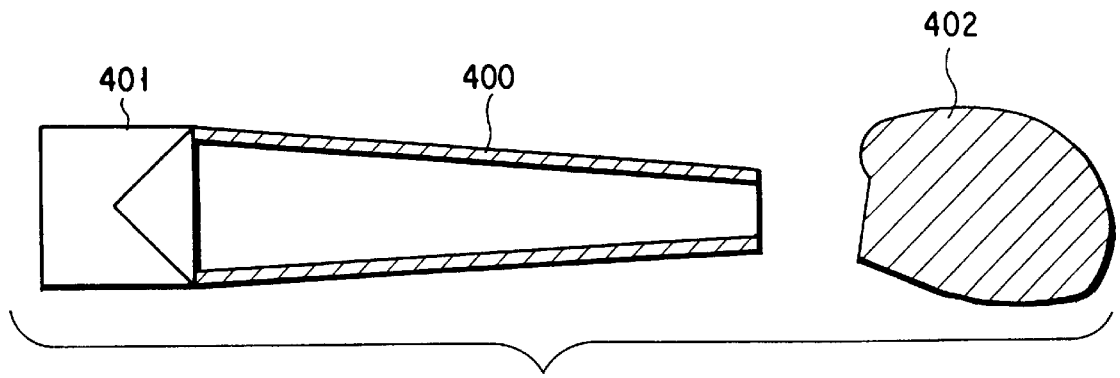
F I G. 11
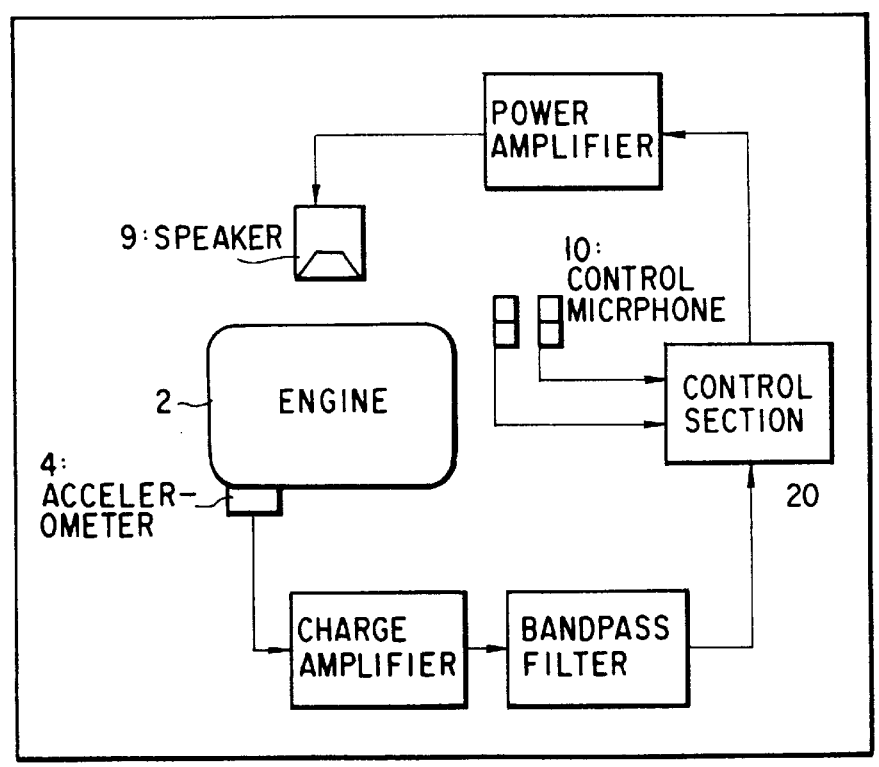
F I G. 13

ACTIVE NOISE CONTROL APPARATUS

BACKGROUND OF THE INVENTION

The present invention relates to an active noise control apparatus, which can reduce noise emitted from devices placed in a three-dimensional space by automatic control, with a simple structure.

As is well-known, in active noise control apparatus, in order to reduce noise emitted from a noise source, an additional sound source is newly provided. Then, an additional sound emitted from the additional sound source and noise are added to each other. By an interference effect of sound generated by the additional sound source and noise, noise is canceled. In such active noise control apparatus, there is often used an additional sound source controlling method. In the method, a synthesized sound of noise and the additional sound is measured by a microphone, and sound pressure is controlled to be zero or minimum.

In the conventional active noise control apparatus, which is used in a system for one-dimensionally propagating sound such as an air-conditioning duct, in order that noise emitted from a noise source can be prevented from being leaked from an opening portion of the air-conditioning duct to the outside, the following arrangement is provided.

More specifically, a reference microphone for obtaining a noise signal propagated through the air-conditioning duct is provided on the noise source side. An estimation microphone for obtaining a signal of sound leaking to the outside from the opening portion is provided on the opening portion side. Moreover, a speaker, serving as an additional sound source, for emitting additional sound to the air-conditioning duct is provided between both microphones.

The signal of sound obtained by the estimation microphone is a signal of a synthesized sound of the sound from the noise source and the sound from the speaker. Sound emitted from the speaker is controlled by an adaptive control device such that the synthesized sound is made close to zero.

The adaptive control device constitutes a control system based on a filter-MLMS algorithm, which is frequently used in an active noise control. The adaptive control device comprises a transfer compensation filter, which is from the speaker to the microphone, an FIR (Finite Impulse Response) filter, and an adaptive FIR filter. More specifically, an output signal of the reference microphone is input to the FIR filter, and input to the adaptive FIR filter through the transfer function compensation filter. An output signal of the estimation microphone is input to the adaptive FIR filter.

The FIR filter obtains a sum of products of the input signal and the filter coefficient, and outputs it. When a sum of the output of the filter and the outer signal is set to be an error signal, the adaptive FIR filter automatically renews the filter coefficient such that the error signal is made close to zero. In this case, the signal from the estimation microphone becomes the error signal. In the Filter-XLMS algorithm, the filter coefficient of the FIR filter is set to be the same as that of the active FIR filter.

Generally, in the adaptive FIR filter, every time when the sampling input is provided, the following calculations are performed:

$$e(n)=d(n)-y(n) \tag{1}$$

$$h(k)^{new}=h(k)^{old}+\mu e(n) \times (n-k+1)(k=1, 2, \ldots, M) \tag{2}$$

In this case, $$y(n) = \sum_{k=1}^{M} h(k)x(n-k+1) \tag{3}$$

In equations (1) to (3), e(n) is an error signal at time n, d(n), y(n) are an outer signal and an output signal of the filter, respectively, and h(k) is a filter coefficient. Also, a mark, new, means a state after the filter coefficient is renewed, a mark, old, means a state before the filter coefficient is renewed. Moreover, x (n−k+1) is an input signal, and $\mu$ is a constant, which is called a step size parameter, which determines a velocity of convergence. Equation (2) showing the renewal of the filter coefficient can be obtained from the following equation (4) of a steepest descent method:

$$h(k)^{new} = h(k)^{old} - \frac{1}{2}\mu \frac{\partial \varepsilon}{\partial h(k)^{old}} (k = 1, 2, \ldots, M) \tag{4}$$

In this case, $$\varepsilon = E[e^2(n)] \text{ ($\varepsilon$ is a square average value of e(N))} \tag{5}$$

$$\frac{\partial \varepsilon}{\partial h(k)^{old}} = -2e(n)x(n-k+1) \tag{6}$$

In the above-mentioned active noise control apparatus, the additional sound for control is emitted from the speaker based on the sound detected by the reference microphone. The additional sound and noise propagated through the air-conditioning duct from the noise source is interfered with each other. Then, sound pressure at the position of the estimation microphone is made close to zero while the degree of interference is being estimated. When a zero point of sound pressure is created, sound is reflected at the point due to a difference in acoustic impedance. As a result, sound is not propagated in the direction of the opening portion, so that noise emitted from the opening portion can be eliminated.

However, such an active noise control apparatus is useful in the system in which noise such as air-conditioning duct is one-dimensionally propagated, but cannot be applied to noise, which is three-dimensionally propagated. The reason can be explained as follows:

In the case of the one-dimensional propagation, only by setting sound pressure at the opening portion, that is, an outlet, to zero, all sound emitted from the noise source can be reflected to prevent sound from being leaked from the outlet. In the case of the three-dimensional propagation, noise is emitted from the noise source all directions. As a result, even if sound pressure is set to zero at one control point, no effect is brought about.

On the other hand, in consideration of the point that noise emitted from devices as the noise sources is three-dimensionally widened, there is proposed the following method for reducing the entire noise from the devices. More specifically, the devices are surrounded by many additional sound sources. Then, each additional sound is emitted from each additional sound source to reduce sound, which is leaked to the outer portion of the surrounded surface. This method is equivalent to the point that the method of one-dimensional propagation of sound in the air-conditioning duct (already explained) is expanded to a three-dimensional space.

In an active noise control apparatus, which can realize the above method, a plurality of additional sound sources is arranged on the surrounded surface with an equal distance. Then, an estimation microphone is provided close to each additional sound source. An output signal of each estimation microphone is input to a controller for drive-controlling each additional sound source. A signal, which is correlated with sound emitted from the devices, such as a vibration signal of a wall surface, is input as a reference signal to the controller through a signal line.

The controller controls each additional sound source such that sound pressure becomes minimum at each estimation microphone. In other words, the controller controls each corresponding additional sound source and the phase such that a sum of squares of sound pressure becomes minimum at each estimation microphone.

However, in the above-structured active noise control apparatus, additional sound emitted from the additional sound sources is mixed with the respective microphones. The control system must be structured to consider influence caused by the mixture of additional sound. As a result, the control system including the controller becomes inevitably complicated. Moreover, the distance between the additional sound sources must be set to be within ½ of the wavelength of sound to be reduced. As a result, a large number of additional sound sources and estimation microphones must be provided when the surrounded surface is set to a position, which is relatively separated from each unit as a noise source.

Moreover, as another method, the following method is proposed to reduce the entire noise from the unit in consideration of the point that noise emitted from the devices as the noise sources is three-dimensionally widened.

More specifically, it is assumed that the devices as noise sources are a set of disperse point sound sources. Then, intensity of these point sound sources and the phase are obtained in advance. Thereafter, intensity of each additional sound source and the phase are controlled such that entire acoustic power becomes minimum when the additional sound sources are arranged. In this case, intensity of the sound source is a volume velocity generated from the sound source, and the volume velocity is obtained by integrating a vibration velocity by its area. Moreover, acoustic power is energy emitted from the sound source per unit time.

In an active noise control apparatus, which can realize the above method, the additional sound source, which is drive-controlled, is provided on each wall surface of each unit as a noise source. It is assumed that disperse sound source exists on each wall surface based on the vibration of each wall surface measured in advance. Then, data base having data prepared in advance is connected to the controller. When noise of each unit as a noise source is added to additional sound of each additional sound source, the controller calculates the phase of each additional sound source and intensity of sound where the entire acoustic power becomes minimum. Then, the controller drive-controls each additional sound source in accordance with the result of the calculation.

In the above-structured active noise control apparatus, it is necessary to obtain amplitude of strength of each sound source and the phase in advance. However, in actual, it is difficult to correctly obtain amplitude of strength of each sound source and the phase. Due to this, there is difficulty in applying this method to the general noise source. Even if amplitude of strength of each sound source and the phase can be obtained, there is complexity in using the apparatus since they must be reset when amplitude of strength of each sound source and the phase are varied halfway. For this reason, such an apparatus does not reach the level of the practical use.

As mentioned above, in the convectional active noise control apparatus, entire noise, which is emitted from the devices placed in three-dimensional space, cannot be effectively reduced by the simple structure.

BRIEF SUMMARY OF THE INVENTION

An object of the present invention is to provide an active noise control device, which can reduce noise radiated from devices placed in a three-dimensional space, by an automatic control, with a simple structure.

According to the present invention, there is provided an active noise control apparatus for controlling a noise caused by a noise source, comprising: a sound source provided close to the noise source; acoustic power measuring means for measuring acoustic power radiated from the sound source as a result of mutual interference between the noise source and the sound source; and controlling means for controlling an output of the sound source such that the acoustic power measured by the measuring means is minimized.

Moreover, according to the present invention, there is provided an active noise control apparatus for controlling noise caused by a noise source, comprising: a sound source located adjacent to the noise source; acoustic intensity measuring means having at least two microphones, provided on same side on a central axis of a vibration surface of the sound source spaced from each other, for measuring an acoustic intensity radiated from the sound source as a result of mutual interference between the noise source and the sound source; and controlling means for controlling an output of the sound source such that the acoustic power measured by the measuring means is minimized.

Further, according to the present invention, there is provided an active noise control apparatus for controlling noise caused by a noise source, comprising: N (where N is an integer) sound sources located adjacent to the noise source; acoustic power measuring means for measuring an acoustic power radiated from the N sound sources as a result of mutual interference between the noise source and the N sound sources; and controlling means for controlling an output of the N sound sources such that the acoustic power measured by the measuring means is minimized.

Furthermore, according to the present invention, there is provided an active noise control method for controlling a noise by driving a sound source provided close to a noise source to cause sound interference between the noise source and the sound source, comprising the steps of: measuring an acoustic power radiated from the sound source as a result of mutual interference between the noise source and the sound source; and controlling an output of the sound source such that the acoustic power measured by the measuring means is minimized.

Further, according to the present invention, there is provided an active noise control method for controlling a noise caused by a noise source emitting sound having a mode including a plurality of loops and nodes, comprising the steps of: providing N (where N is an integer) sound sources at a position of the loop of the mode; measuring N acoustic power radiated from each of the sound source as a result of mutual interference between the noise source and each sound source; and controlling outputs of the N sound sources such that the N acoustic power measured by these measuring means is set to be zero or minimized.

According to the above-structured active noise control apparatus and method, acoustic power radiated from the sound source is controlled to be minimized, so that the total acoustic power of the noise source and the sound source can be minimized. As a result, noise radiated from the noise source to the portion around the noise source can be effectively reduced, and this largely contributes to the reduction of sound.

Further, according to the present invention, there is provided a stand-alone power generator having an active noise control apparatus for controlling noise from an engine driving a generator, comprising:

a sound source located adjacent to the engine;

acoustic power measuring means for measuring an acoustic power radiated from the sound source as a result of mutual interference between sound of the engine and the sound source; and controlling means for controlling an output of the sound source such that the acoustic power measured by the measuring means is minimized.

Moreover, according to the present invention, there is provided a transformer in an active noise control apparatus for controlling noise from a tank containing a core, a coil, and insulating oil, comprising:

a sound source located adjacent to the tank;

acoustic power measuring means for measuring an acoustic power radiated from the sound source as a result of mutual interference between noise from the tank and sound of the sound source; and controlling means for controlling an output of the sound source such that the acoustic power measured by the measuring means is minimized.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 is a block diagram showing an outline structure of an active noise control apparatus according to a fourth embodiment of the present invention;

FIG. 6 is a view explaining a controlling process by adaption controlling means according to the fourth embodiment of the present invention;

FIG. 7 is a view explaining a controlling process by adaption controlling means according to the fourth embodiment of the present invention;

FIG. 11 is a cross-sectional view showing an additionally provided device to the active noise control apparatus according to a seventh embodiment of the present invention;

FIG. 13 is a block diagram showing the outline structure of the active nose control apparatus applied to the private power generator according to the eighth embodiment of the present invention;

DETAILED DESCRIPTION OF THE INVENTION

Embodiments of the present invention will now be described with reference to the accompanying drawings.

First Embodiment

Figure 1:
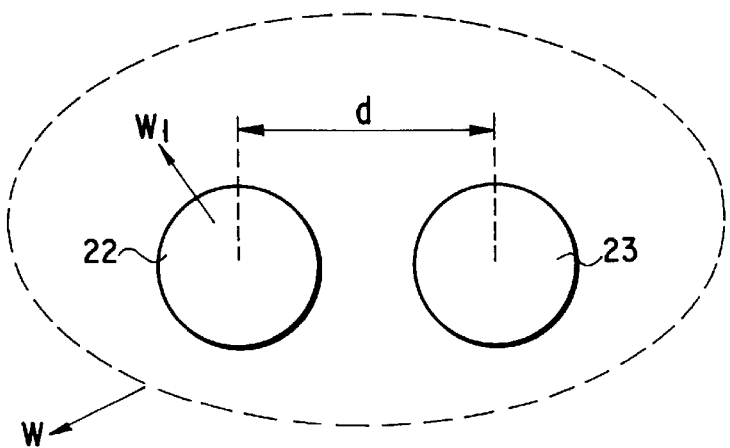
FIG. 1 is a view showing a model of each of a noise source and an additional sound source according to a first embodiment of the present invention.

FIG. 1 shows a first embodiment of the present invention explaining a basic concept of noise eliminating means which the active noise control apparatus of the present invention comprises.

As one of methods for reducing acoustic power of sound radiated from a noise source, there is known a method in which additional sound source, which has amplitude equal to the noise source and a phase opposite to the noise source, is placed close to the noise source. In this case, sound radiated from the noise source is interfered with sound radiated from the additional sound source, and they cancel each other. As a result, acoustic power can be reduced.

It is assumed that a simple model shown in FIG. 1 is considered. In FIG. 1, reference numeral 22 is a noise source, and reference numeral 23 is an additional sound source. Both sources emit sound having an angular frequency ω. It is assumed that intensity of sound from the additional sound source 23 has the same amplitude as sound from the noise source 22 and its phase is opposite to the phase of the noise source 22. If acoustic power is set to W1 when only noise source 22 emits sound and a sum of acoustic power when both sources emit sound is $W^0$ and its ratio is set to γ, the following equation can be established:

$$\gamma = \frac{W}{W_1} = 2\{1 - \sin c(kd)\} \quad (7)$$

In this case, sin c() is a function defined as sin c(x)=sin(x)/x, k is wave number of sound, k=ω/c when a sound velocity is c, and d is a distance between the noise source 22 and the additional sound source 23. In equation (7), the case of γ=1 shows that acoustic power, which is measured after the additional sound source 23 emits sound, is equal to acoustic power, which is measured when only the noise source 22 emits sound.

However, according to this method, if distance d is near to a half of the wavelength of sound, all acoustic power is increased more than acoustic power measured when only the noise source 22 emits sound. This is not suitable for a condition of minimizing acoustic power.

The condition of minimizing acoustic power is that radiated acoustic power of the additional sound source 23 becomes zero. This does not means that the additional sound source 23 is set to a stationary state not to emit sound. In other words, this means the following state:

Specifically, the phase between the particle velocity of the additional sound source 23 and the sound pressure on the surface is shifted at 90°. Then, energy of sound radiated from the sound source and that of sound flowing to the sound source are balanced to be zero. When acoustic power is minimum, ratio γ of acoustic power before the addition sound source 23 sounds to acoustic power after the addition sound source 23 sounds can be obtained as following equation:

$$\gamma = \frac{W}{W_1} = 1 - \{\sin c(kd)\}^2 \quad (8)$$

As a result, even if the additional sound source 23 sounds, acoustic power is not increased more than acoustic power measured when only the noise source 22 emits sound.

According to the present invention, entire acoustic power W can be obtained by the following equation:

$$W = W_Q + W_{qQ} + W_{Qq} + W_q \quad (9)$$

wherein acoustic power of single additional sound source is $W_Q$, acoustic power of single noise source is $W_q$ ($W_1$), acoustic power of the addition sound source, which is obtained when the sound of the noise source and that of the additional sound source are interfered with each other, is $W_{qQ}$, and that of the noise source, which is obtained when the sound of the noise source and that of the additional sound source are interfered with each other, is $W_{Qq}$.

Then, as shown in the following equation (10), when acoustic power Wa of the additional sound source is zero, the total acoustic power W becomes minimum.

$$W_a = W_Q + W_{qQ} = 0 \quad (10)$$

Acoustic power $W_a$ of the additional sound source is obtained, and the additional sound source is controlled such that acoustic power Wa becomes minimum. Thereby, the total acoustic power can be minimized.

As explained above, acoustic power of the sound source (noise source, additional sound source) is energy radiated from the sound source per unit time. This can be obtained by integrating acoustic intensity radiated from the sound source by the entire surfaces surrounding the sound source. Acoustic intensity is energy of sound passing a unit area for unit time.

Then, according to the present invention, acoustic intensity as an estimation value of acoustic power is measured, and controlled to be zero or minimized. In general, a speaker is used as an additional sound source, and the speaker is considered as a point sound source. Due to this, if acoustic intensity is measured at the position close to the speaker on substantially a central axis of the vibration axis, a value, which is proportional to acoustic power, can be obtained. Thereby, data, which is necessary for minimizing acoustic power, can be obtained.

There are several methods for measuring acoustic intensity of sound radiated from the additional sound source. A two-microphone method is the easiest. Acoustic intensity can be obtained by time averaging a product of sound pressure and a particle velocity of a medium, and the particle velocity is proportional to a value, which is obtained by differentiating sound pressure by the distance. Sound pressure can be measured by the microphone. However, the particle velocity cannot be measured by the microphone. According to the two-microphone method, sound pressure is measured by each of two microphones placed close to each other, and the particle velocity is obtained based on the differential result.

Thus, if acoustic intensity of the additional sound source is controlled to be zero, acoustic power of the additional sound source can be zero. Also, the total acoustic power having acoustic power of the noise source and that of the additional sound source added to each other can be reduced. According to this method, sound, which is three-dimensionally propagated from the noise source, can be reduced in the range of the entire surroundings of the noise source instead of controlling sound pressure to be zero at one point.

As explained above, according to the present invention in which the additional sound source is provided close to the noise source, acoustic power ($W_a = W_Q + W_{qQ}$) radiated from the additional sound source as a result of mutual interference between the noise source and the additional sound source, thereby controlling the output of the additional sound source such that acoustic power to be measured to be zero or minimized, the total acoustic power having acoustic power of the noise source and that of the additional sound source added to each other can be reduced. According to this method, sound, which is three-dimensionally propagated from the noise source, can be reduced in the range of the entire surroundings of the noise source instead of controlling sound pressure to be zero at one point.

Second Embodiment

Next, the following will explain a second embodiment of the present invention.

Figure 2:
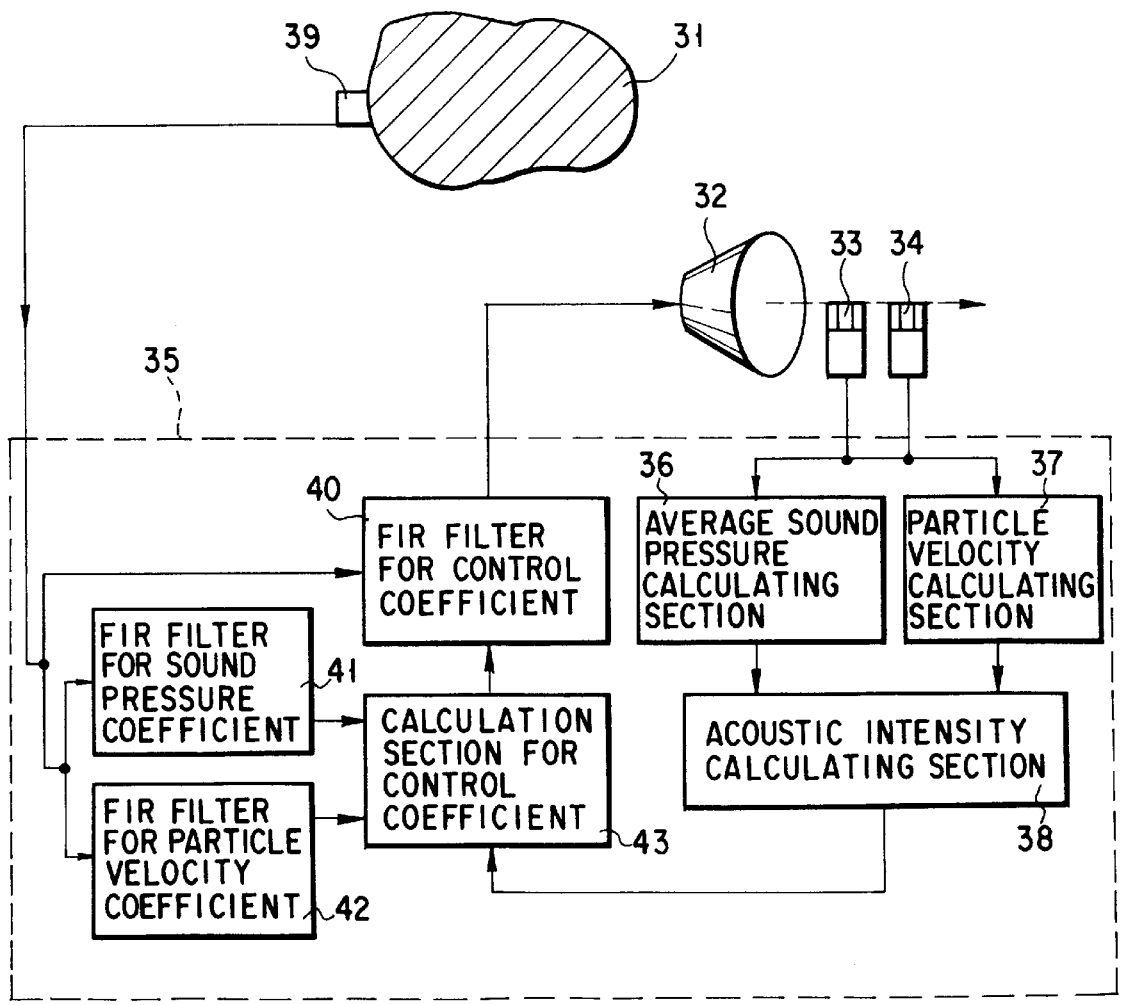
FIG. 2 is a block diagram showing an outline structure of an active noise control apparatus according to a second embodiment of the present invention.

FIG. 2 is a block diagram showing an outline structure of an active noise control apparatus according to the second embodiment of the present invention.

In the figure, reference numeral 31 is an object unit such as a transformer arranged three-dimensionally, that is, a noise source. A speaker 32, serving as an additional sound source, is provided close to the noise source 31. Two microphones 33 and 34 are provided on a central axis of the vibration surface of the speaker 32 to have a predetermined distance. A sound pressure signal, which is measured by each of microphones 33 and 34, is introduced to a controller 35.

The controller 35 comprises an average sound pressure calculating section 36 for obtaining average sound pressure between the microphones from the sound pressure signal of each of the microphones 33 and 34, and a particle velocity calculating section 37 for obtaining a particle velocity. Average sound pressure data and particle velocity data, which are obtained by the calculating sections 36 and 37, are introduced to an acoustic intensity calculating section 38. The acoustic intensity calculating section 38 obtains acoustic intensity based on both data.

An accelerometer 39 for obtaining a reference signal, which is correlated with generating noise, is attached onto a wall surface of the noise source 31. The reference signal obtained by the accelerometer 39 is sent to the controller 35.

On one hand, the reference signal is introduced to an FIR filter 40 for a control coefficient. At this time, the reference signal is multiplied by a control coefficient to serve as an input signal for the speaker 32. On the other hand, the reference signal is further divided to two. One is introduced to an FIR filter 41 for a sound pressure coefficient from the speaker 32 obtained by the microphone 33 and 34, and the other is introduced to an FIR filter 42 for a particle velocity coefficient from the speaker 32 obtained by the microphones 33 and 34. Then, a sum of products of each reference signal and the original signal is calculated, and the result is sent to a calculation section 43 for a control coefficient.

The calculation section 43 renews the control coefficient (filter coefficient) of the FIR filter 40 such that acoustic intensity emitted from the speaker 32 by filter-X LMS algorithm is near zero. In other words, the error signal was sound pressure in the conventional case. In the above-explained second embodiment, the error signal is acoustic intensity, and the control coefficient of FIR filter 40 is renewed such that the value is near zero, sequentially.

The renewal of the control coefficient can be executed based on the following equation (11), which is the same as equation (4).

$$h(k)^{new} = h(k)^{old} - \frac{1}{2}\mu \frac{\partial I(n)^2}{\partial h(k)^{old}} \quad (k = 1, 2, \ldots, M) \quad (11)$$

According to the above-mentioned structure, since acoustic power emitted from the speaker 32 as an additional sound source can be near zero, the entire acoustic power, which has the noise source and the additional sound source added to each other, can be reduced. Thereby, a good elimination effect can be brought about.

If the noise source generates large acoustic noise (to be specially explained later), a plurality of additional sound sources is provided to the noise source. In this case, it is required that outputs from the additional sound sources be simultaneously controlled.

Third Embodiment

Next, the following will explain a third embodiment.

In the first embodiment, only one speaker as an additional sound source was provided. However, there is a case in which noise whose mode is different occurs at a plurality of locations. The third embodiment is applied to such a noise source. Specifically, the additional sound sources are provided to correspond to the respective modes, and an acoustic intensity measuring section is provided in each additional sound source. Then, acoustic power radiated from each additional sound source is controlled to be zero or minimized, thereby obtaining a noise reduction effect.

Figure 3:
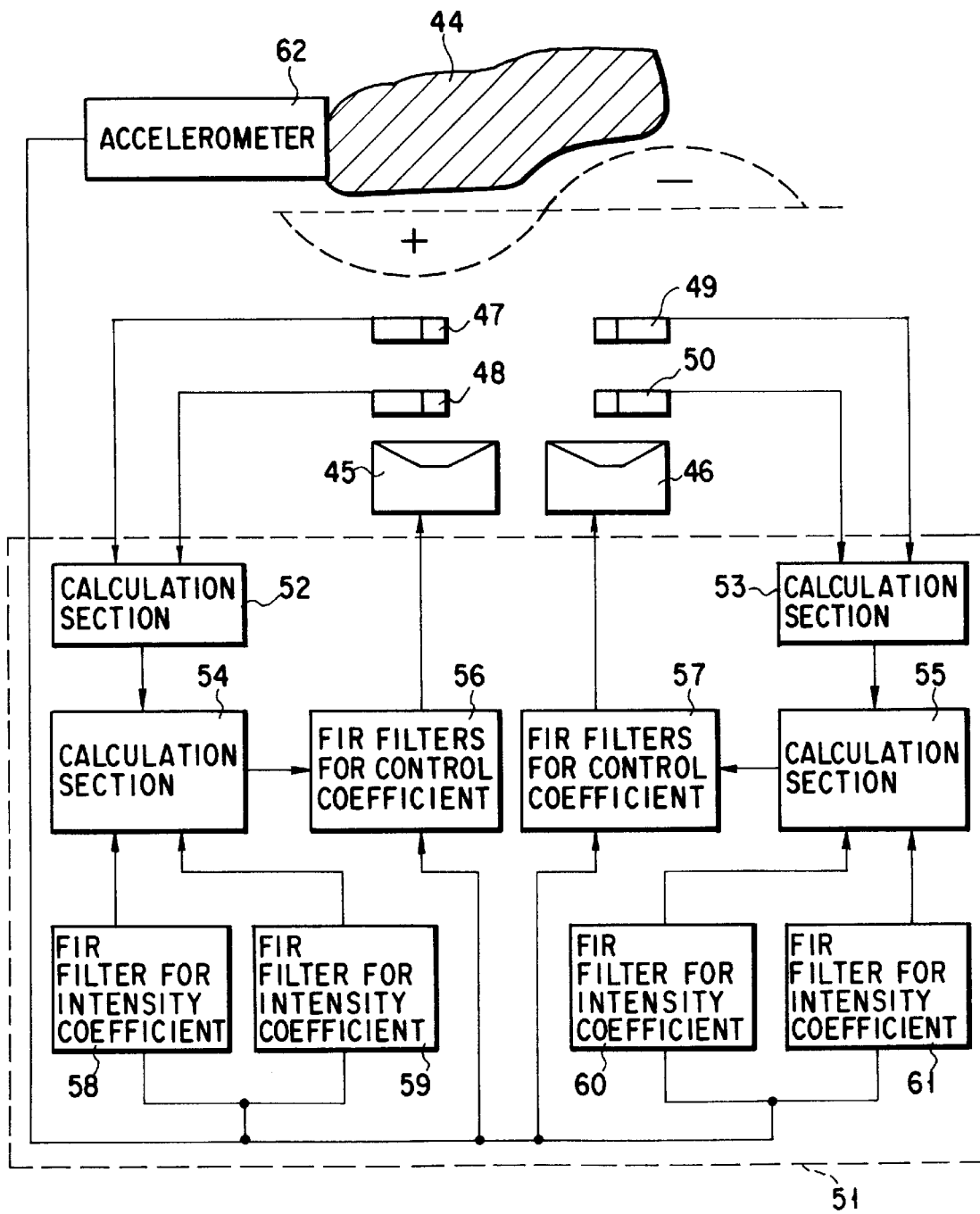
FIG. 3 is a block diagram showing an outline structure of an active noise control apparatus according to a third embodiment of the present invention.

FIG. 3 is a block diagram showing an outline structure of an active noise control apparatus according to the third embodiment of the present invention.

In the figure, reference numeral 44 is an object unit such as a transformer arranged three-dimensionally, that is, a noise source. The noise source 44 comprises a mode having a loop (maximum amplitude) and a node (minimum amplitude).

FIG. 3 explains the case in which the mode of the noise source 44 has two loops. This embodiment explains a control method for reducing amplitude of two loops, simultaneously.

A speaker 45 is provided at a loop position close to the noise source 44, and a speaker 46 is provided at a loop next thereto.

Two microphones 47 and 48 are provided on a central axis of the vibration surface of the speaker 45 to have a predetermined distance. Also, two microphones 49 and 50 are provided on a central axis of the vibration surface of the speaker 46 to have a predetermined distance. A sound pressure signal measured by the microphones 47 and 48 and a sound pressure signal measured by the microphones 49 and 50 are introduced to a controller 51.

The controller 51 comprises calculation sections 52 and 53, which calculate average sound pressure between the microphones based on the sound signals, and acoustic intensity, which is the time average of particle velocity.

An accelerometer 62 for obtaining a reference signal, which is correlated with generating noise, is attached to the noise source 44. The reference signal obtained by the accelerometer 39 is sent to the controller 62.

On one hand, the reference signal is introduced to FIR filters 56 and 57 for a control coefficient. At this time, the reference signal is multiplied by a control coefficient to serve as an input signal for each of the speakers 45 and 46. On the other hand, the reference signal is further divided to four. The divided reference signals are introduced to an FIR filter 58 for an intensity coefficient from the speaker 45 obtained by the microphones 47 and 48, an FIR filter 59 for an intensity coefficient from the speaker 46 obtained by the microphones 47 and 48, an FIR filter 60 for an intensity coefficient from the speaker 45 obtained by the microphones 49 and 50, and an FIR filter 61 for an intensity coefficient from the speaker 46 obtained by the microphones 49 and 50, respectively. Then, a sum of products of each reference signal and the original signal is calculated, and the result is sent to calculation sections 54 and 55 for a control coefficient.

The calculation sections 54 and 55 renew the control coefficients (filter coefficient) of the FIR filters 56 and 57 such that acoustic intensity emitted from the speakers 45 and 46 by filter-XLMS algorithm is simultaneously near zero.

The renewal of the control coefficient can be executed based on the following equation (12) in which equation (11) is expanded.

$$h_m(K)^{new} = h_m(K)^{old} - \frac{1}{2}\mu \sum_{l=1}^{L} \frac{\alpha I_{lm}(n)^2}{\alpha h(K)^{old}} \quad (K = 1, 2, \ldots, M) \quad (12)$$

wherein hm is a m-th filter coefficient, $\mu$ is a coefficient of a convergent ratio, and Ilm is intensity from a m-th speaker detected by a l-th microphone.

According to the above-mentioned structure, since acoustic power emitted from the speakers 45 and 46 as additional sound sources can be simultaneously near zero, the entire acoustic power, which has the noise source with a mode and the additional sound sources added to each other, can be reduced. Thereby, a good elimination effect can be brought about.

If the noise source generates large acoustic noise (to be specially explained later), a plurality of additional sound sources is provided to the noise source. In this case, it is required that outputs from the additional sound sources be simultaneously controlled. In the above third embodiment, a plurality of speakers, which are simultaneously controlled, is provided to correspond to the speaker 45, and a plurality of speakers, which are simultaneously controlled, is provided to correspond to the speaker 46.

Fourth Embodiment

FIG. 4 is a block diagram showing an outline structure of an active noise control apparatus according to the fourth embodiment of the present invention.

In the figure, reference numeral 63 is an object unit such as a transformer arranged three-dimensionally, that is, a noise source. The noise source 63 comprises a mode having a loop (maximum amplitude) and a node (minimum amplitude).

FIG. 4 explains the case in which the mode of the noise source 63 has two loops. This embodiment explains a control method for reducing the loops one by one.

At least one speaker 46 is provided at a loop position close to the noise source 63, and at least one or more speaker 65 is provided at a loop next thereto.

Two microphones 66 and 67 are provided on a central axis of the vibration surface of the speaker 64 to have a predetermined distance. Also, two microphones 68 and 69 are provided on a central axis of the vibration surface of the speaker 65 to have a predetermined distance. A sound pressure signal measured by the microphones 66 and 67 and a sound pressure signal measured by the microphones 68 and 69 are introduced to a controller 70.

The controller 70 comprises calculation sections 71 and 72, which calculate average sound pressure between the microphones based on the sound signals, and acoustic intensity, which is the time average of particle velocity.

An accelerometer 80 for obtaining a reference signal, which is correlated with generating noise, is attached to the noise source 63. The reference signal obtained by the accelerometer 80 is sent to the controller 70.

On one hand, the reference signal is introduced to an FIR filter 74 for a control coefficient provided in an adaption control calculation section 75. At this time, the reference signal is multiplied by a control coefficient to serve as an input signal for the speaker 64 or 65. On the other hand, the reference signal is further divided. The divided reference signals are introduced to an FIR filter 78 for an intensity coefficient from the speaker 64 obtained by the microphones 66 and 67, and an FIR filter 79 for an intensity coefficient from the speaker 65 obtained by the microphones 68 and 69, respectively. Then, a sum of products of each reference signal and the original signal is calculated, and the result is sent to the calculation section 74 for a control coefficient.

The feature of the above system lies in the following point:

Specifically, unlike the apparatus of the second embodiment, the number of the adaption control calculation section 75, which comprises the calculation section for a control coefficient and the FIR filter for a control coefficient, may be one even if the number of additional sound sources is increased in accordance with the increase in the number of the loops.

The following will explain the control steps by the single adaption control calculation section:

Step 1

A loop on the left side on paper is controlled. The speaker 64 provided close to the loop, the microphones 66 and 67, and the accelerometer 80 are used to reduce acoustic power of one loop.

To realize the above object, all signal switching sections 81, 82, 83, and 84 are set to ① sides.

Figure 5:
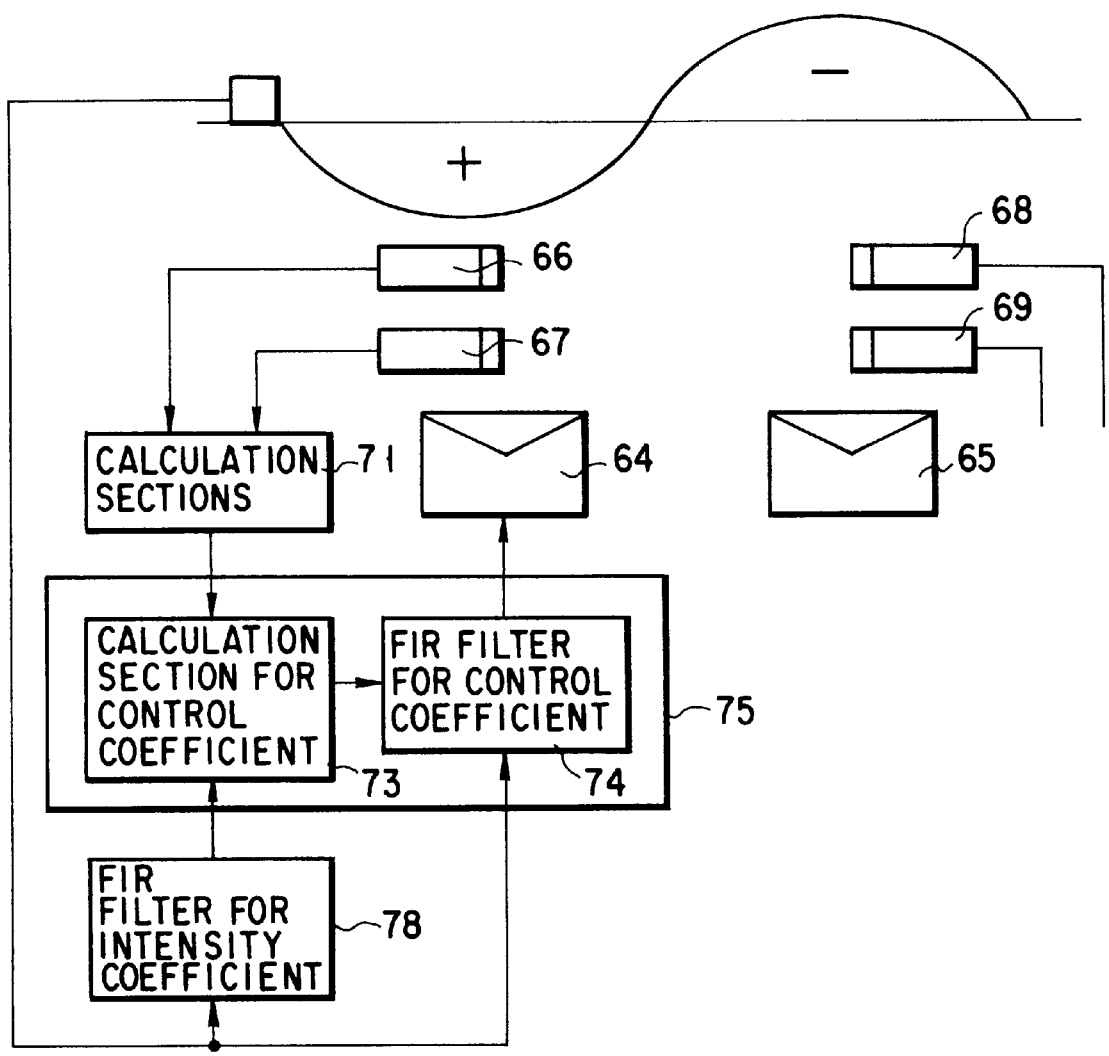
FIG. 5 is a view explaining a controlling process by adaption controlling means according to the fourth embodiment of the present invention.

This corresponds to FIG. 5, and sound is emitted from only the speaker 64. The merits of this method lies in the following point:

Specifically, even if the speaker is shifted from the most effective position, a solution for minimizing the total acoustic power can be found, and an optimum output (amplitude, phase) is executed. As a result, sound is not inversely increased at a different location.

Therefore, even if the left loop is controlled, unfavorable influence is not exerted on sound on the right loop (oppose phase surface). At the worst, the right loop is unchanged, and sound is not inversely increased.

Then, the adaption control can be executed from the large sound area in order. The adaption control is ended when acoustic power from the speaker 64 is zero or minimized. The control coefficient obtained by the adaption control calculation section is sent to an FIR calculation section for a fixed coefficient. As a result, sound having a constant amplitude and phase characteristic is emitted from the speaker 64.

Step 2

The loop on the right side, which is not still reduced in step 1, is controlled. The speaker 65 provided close to the loop, the microphones 68 and 69, and the accelerometer 80 are used to reduce acoustic power of one loop.

To realize the above object, all signal switching sections 81, 82, 83, and 84 are set to ② sides.

This corresponds to FIG. 6, and the right loop is reduced by the speaker 65. At this time, sound is emitted from the speaker 65. However, even in a state that the speaker is provided, a solution for minimizing the entire acoustic power can be found, and an optimum output (amplitude, phase) can be executed. As a result, the right loop can be reduced without having unfavorable influence of the speaker 64, and the left sound reduced in step 1 is not increased.

The adaption control is ended when acoustic power from the speaker 65 is zero or minimized. In this case, an acoustic power component from the speaker 64 is superimposed on the microphones 68 and 69 provided to measure acoustic power from the speaker 65. However, this does not lead to the large deterioration since direct sound from the speaker 65 has a great influence on the reduction of the total acoustic power.

Step 3

The control coefficient obtained by the adaption control calculation section 75 is sent to an FIR calculation section 77 for a fixed coefficient. As a result, as shown in FIG. 7, sound having a constant amplitude and phase characteristic is radiated from the speaker 65.

If the noise source generates large acoustic noise (to be specially explained later), a plurality of additional sound sources is provided to the noise source. In this case, it is required that outputs from the additional sound sources be simultaneously controlled.

Fifth Embodiment

FIG. 5 is a block diagram showing an outline structure of an active noise control apparatus according to the fifth embodiment of the present invention.

In the figure, reference numeral 85 is s noise source such as an engine placed in a mechanical chamber (closed space) of a private power generator. Sound radiated from the noise source 85 exists as a standing wave in a closed space 86.

Figure 8:
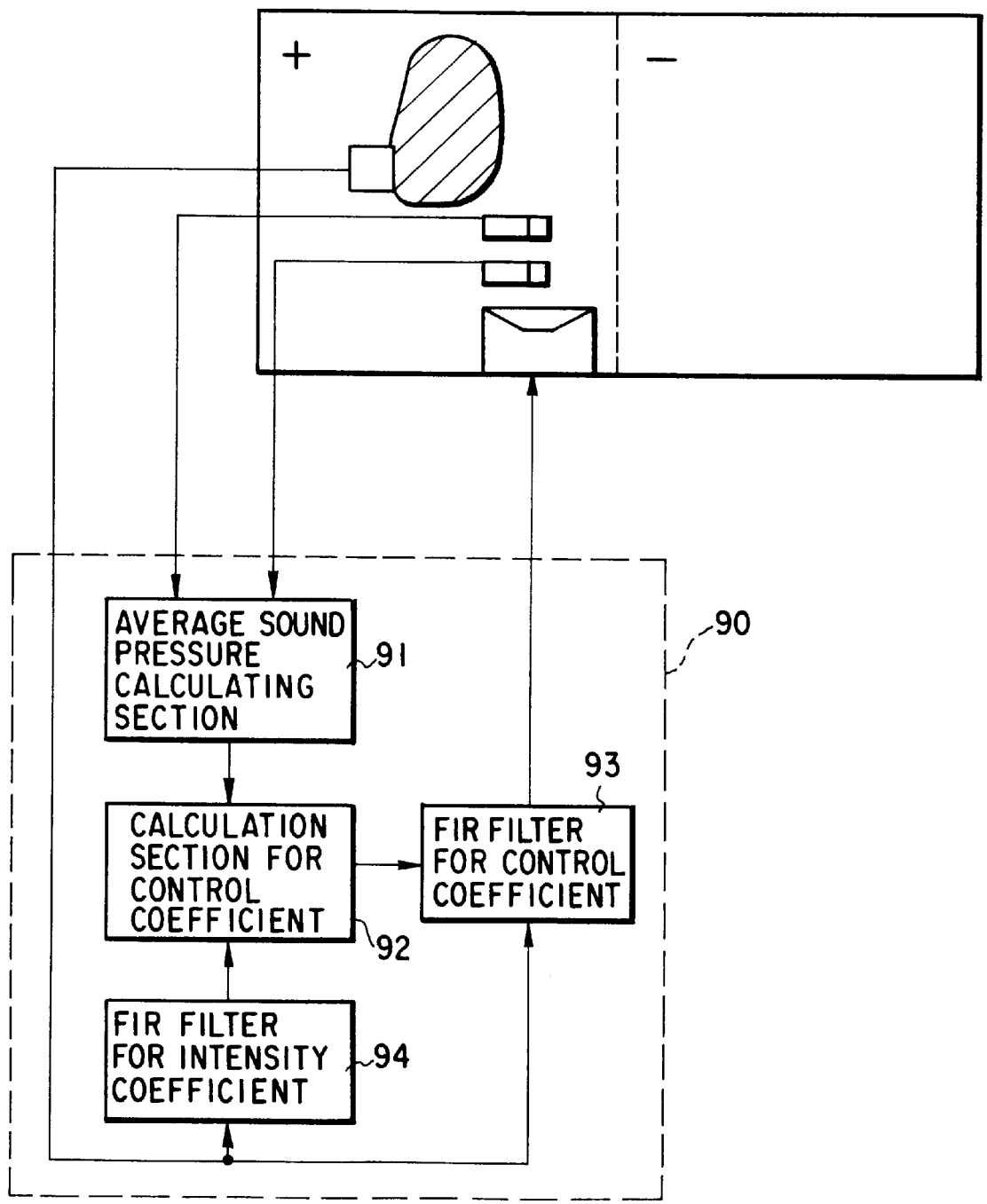
FIG. 8 is a block diagram showing an outline structure of an active noise control apparatus according to a fifth embodiment of the present invention.

This embodiment relates to a noise reducing method when N standing waves are excited in the closed space 86. FIG. 8 shows a case in which the mode having two loops is excited. The following will explain the noise reducing method of this embodiment with reference to FIG. 8.

A speaker 87 is made close to the noise source 85 so as to be placed at the position of the same phase of the mode to be controlled.

Acoustic emission power generated from the additional sound source with a speaker as a result of mutual interference between the noise source and the additional sound source. Thereby, an output from the speaker 87 is controlled such that measuring acoustic power is set to be zero or minimized.

Two microphones 88 and 89 are provided on a central axis of the vibration surface of the speaker 87 to have a predetermined distance. A sound pressure signal, which is measured by each of microphones 88 and 89, and a particle velocity signal are introduced to a controller 90.

The controller 90 comprises an average sound pressure calculating section 91, which calculates average sound pressure between the microphones based on the sound pressure signal of each of the microphones 88 and 89 and acoustic intensity, which is the time average of particle velocity.

An accelerometer 95 for obtaining a reference signal, which is correlated with generating noise, is attached to the noise source 85. The reference signal obtained by the accelerometer 95 is sent to the controller 90.

On one hand, the reference signal is introduced to an FIR filter 93 for a control coefficient. At this time, the reference signal is multiplied by a control coefficient to serve as an input signal for the speaker 87. On the other hand, the reference signal is further divided into two. These signals are introduced to an FIR filter 94 for an intensity coefficient from the speaker obtained by the microphones 88 and 89. Then, a sum of products of each reference signal and the original signal is calculated, and the result is sent to a calculation section 92 for a control coefficient.

The calculation section 92 renews the control coefficient (filter coefficient) of the FIR filter 93 such that acoustic intensity emitted from the speaker 32 by filter-X LMS algorithm is near zero.

According to the above-mentioned structure, acoustic power radiated from the speaker 87 as an additional sound source can be near zero, acoustic power of the closed space where the mode is excited can be reduced, and a good elimination effect can be brought about. Unlike the free space, in the closed space, the modes are superimposed on each other. However, the output characteristic of the addition sound source, which is obtained when the total acoustic power (equation (a) set forth below) becomes minimum, can be obtained by equation (b) set forth below.

Equation (a) is shown as follows:

$$W = \frac{1}{2} \frac{\omega^2 \rho c^2}{V} \sum_r p 2\xi_r \frac{\omega_r}{M_r\{(\omega_r^2 - \omega^2)^2 + (2\xi_r\omega_r\omega)^2\}} \times \quad \text{equation (a)}$$

$$\left\{|q_p|^2\{\varphi_r(x_p)\}^2 + |q_{sl}|^2 \sum_{i=1}^{N}\sum_{j=1}^{N} \varphi_r(x_{si})\varphi_r(x_{sj}) + \right.$$

$$\left. 2\sum_{i=1}^{N} |q_p q_{sl}| \varphi_r(x_p)\varphi_r(x_{si})\cos(\theta_{sl} - \theta_p)\right\}$$

wherein $\omega = 2\pi f/c$ (angular frequency), V: volume, c: sound velocity, $\rho$: density, $\omega_r$=natural frequency, Qp: intensity of sound source, $q_{si}$ (i=1, 2, . . . N): intensity of N additional sound sources, natural mode $$\phi : \varphi_r := \cos\left(\frac{\pi}{a}ix\right)\cos\left(\frac{\pi}{b}jy\right)\cos\left(\frac{\pi}{c}kz\right) \; (i, j, k = 0, 1, 2, \ldots, \infty),$$

$\theta_p$: phase of sound source, $\theta_{si}$: phase of additional sound source, Mr: modal mass, and $\xi_r$: modal damping.

The condition for minimizing the total acoustic power of the closed space can be obtained as follows:

$$\sum_{i=1}^{N} \varphi_r(x_p)\varphi_r(x_{si}) > 0$$

It is assumed that the additional sound source is made close to the sound source to be placed at the position of the same phase of the mode. If N additional sound sources are controlled at the same phase, $\theta_{sl}=\theta_{si}$ (i=1, 2, . . . N). Therefore, the output characteristic of the additional sound source for minimizing the power can be obtained by the following equation (b):

$$\begin{cases} 'Q_{sl} - Q_p = \pi & \text{equation (b)} \\ \frac{q_s}{q_p} = \frac{\displaystyle\sum_r \frac{\xi_r\omega_r}{M_r} \frac{\sum_{i=1}^{N}\varphi_r(x_p)\varphi_r(x_{si})}{(\omega_r^2 - \omega^2)^2 + (2\xi_r\omega_r\omega)^2}}{\displaystyle\sum_r \frac{\xi_r\omega_r}{M_r} \frac{\sum_{i=1}^{N}\sum_{j=1}^{N}\varphi_r(x_{si})\varphi_r(x_{sj})}{(\omega_r^2 - \omega^2)^2 + (2\xi_r\omega_r\omega)^2}} \end{cases}$$

At this time, acoustic power (shown in the following equation (13)), which is generated from the additional sound source as result of the mutual interference between the additional sound source and the sound source, becomes zero.

$$\frac{1}{2} \frac{\omega^2 \rho c^2}{V} \sum_r \frac{2\xi_r\omega_r}{M_r\{(\omega_r^2 - \omega^2)^2 + (2\xi_r\omega_r\omega)^2\}} \times \quad (13)$$

-continued $$\left\{|q_{sl}|^2 \sum_{i=1}^{N}\sum_{j=1}^{N}\varphi_r(x_{si})\varphi(x_{sj}) + \sum_{i=1}^{N}|q_p q_{sl}|\varphi_r(x_p)\varphi_r(x_{si})\cos(Q_{sl}-Q_p)\right\}$$

Therefore, if the acoustic power can be set to be zero or minimized, the entire power can be reduced.

If the noise source generates large acoustic noise (to be specially explained later), a plurality of additional sound sources is provided to the noise source. In this case, it is required that outputs from the additional sound sources be simultaneously controlled.

Sixth Embodiment

Figure 9:
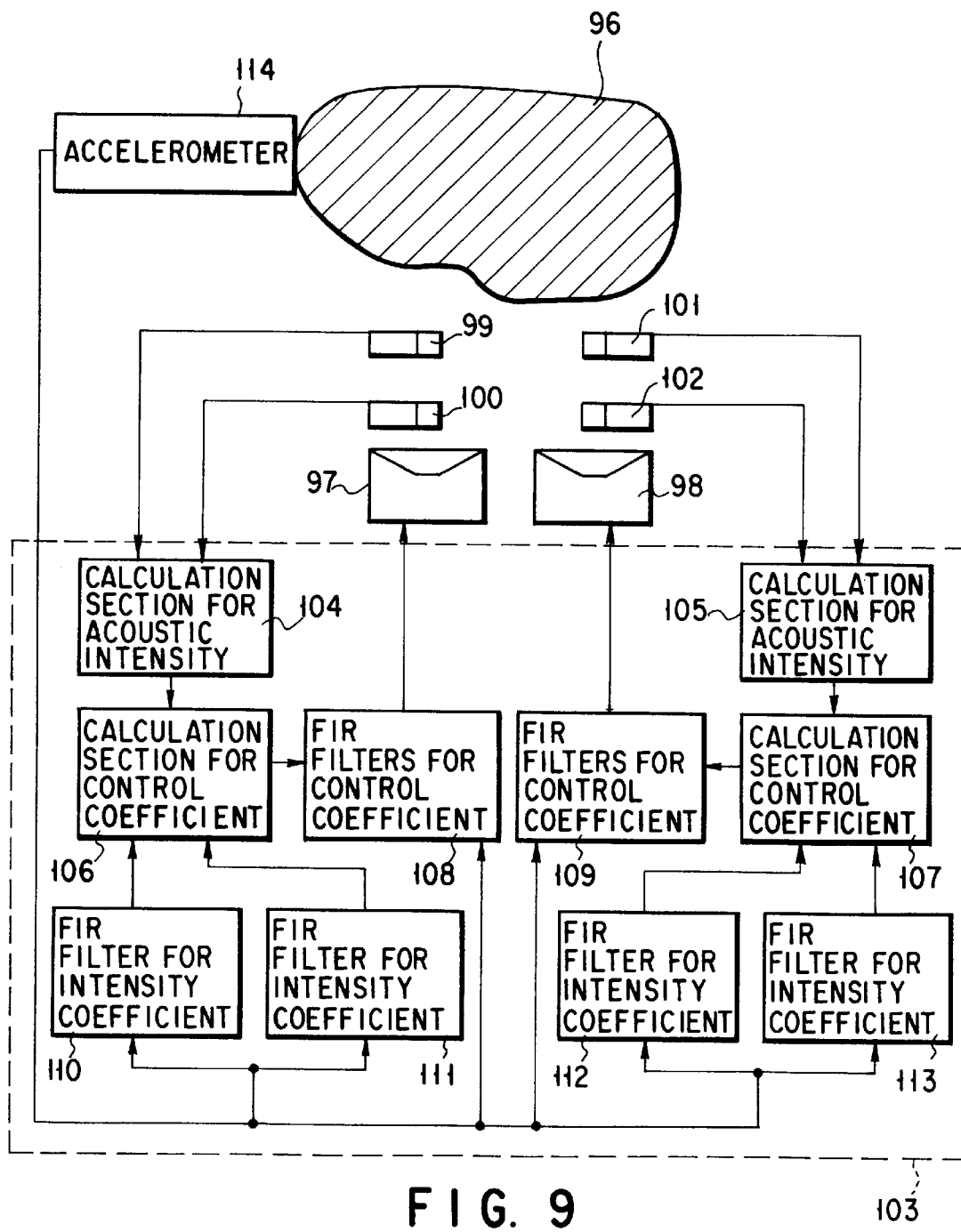
FIG. 9 is a block diagram showing an outline structure of an active noise control apparatus according to a sixth embodiment of the present invention.
Figure 10A:
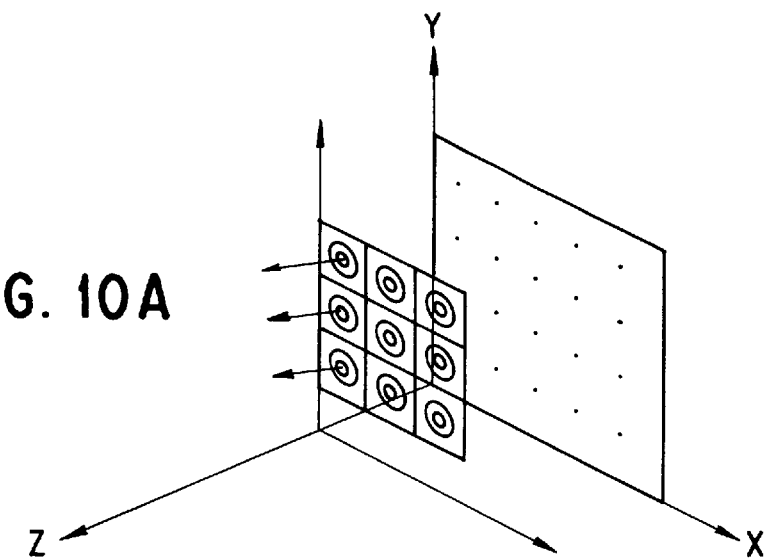
FIG. 10A is a perspective view schematically showing a state that a plurality of additional sound sources are arranged in a matrix form to be opposite to wall surfaces according to the sixth embodiment of the present invention.
Figure 10B:
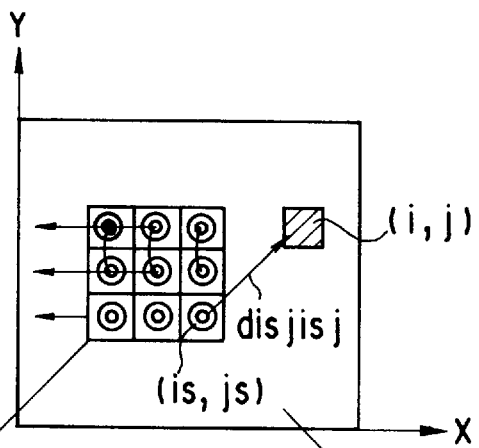
FIG. 10B is a view schematically showing a state that a plurality of additional sound sources are arranged in a matrix form to be opposite to wall surfaces, seeing from a Z-axial direction, according to the sixth embodiment of the present invention.
Figure 10C:
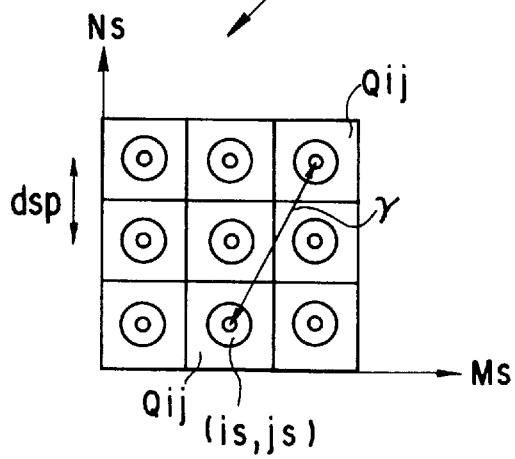
FIG. 10C is a perspective view schematically showing a coordinate system of the additional sound source in state that a plurality of additional sound sources are arranged in a matrix form to be opposite to wall surfaces according to the sixth embodiment of the present invention.
Figure 10D:
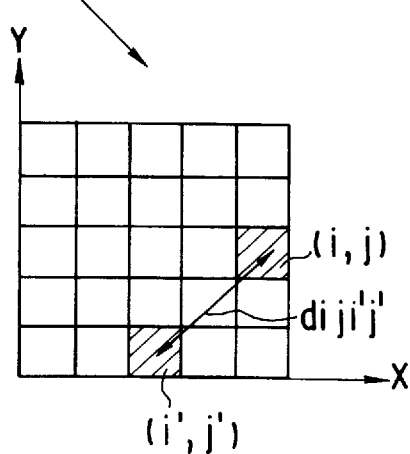
FIG. 10D is a view schematically showing a state that a plurality of additional sound sources are arranged in a matrix form to be opposite to wall surfaces, seeing from a Z-axial direction, according to the sixth embodiment of the present invention.
Figure 12:
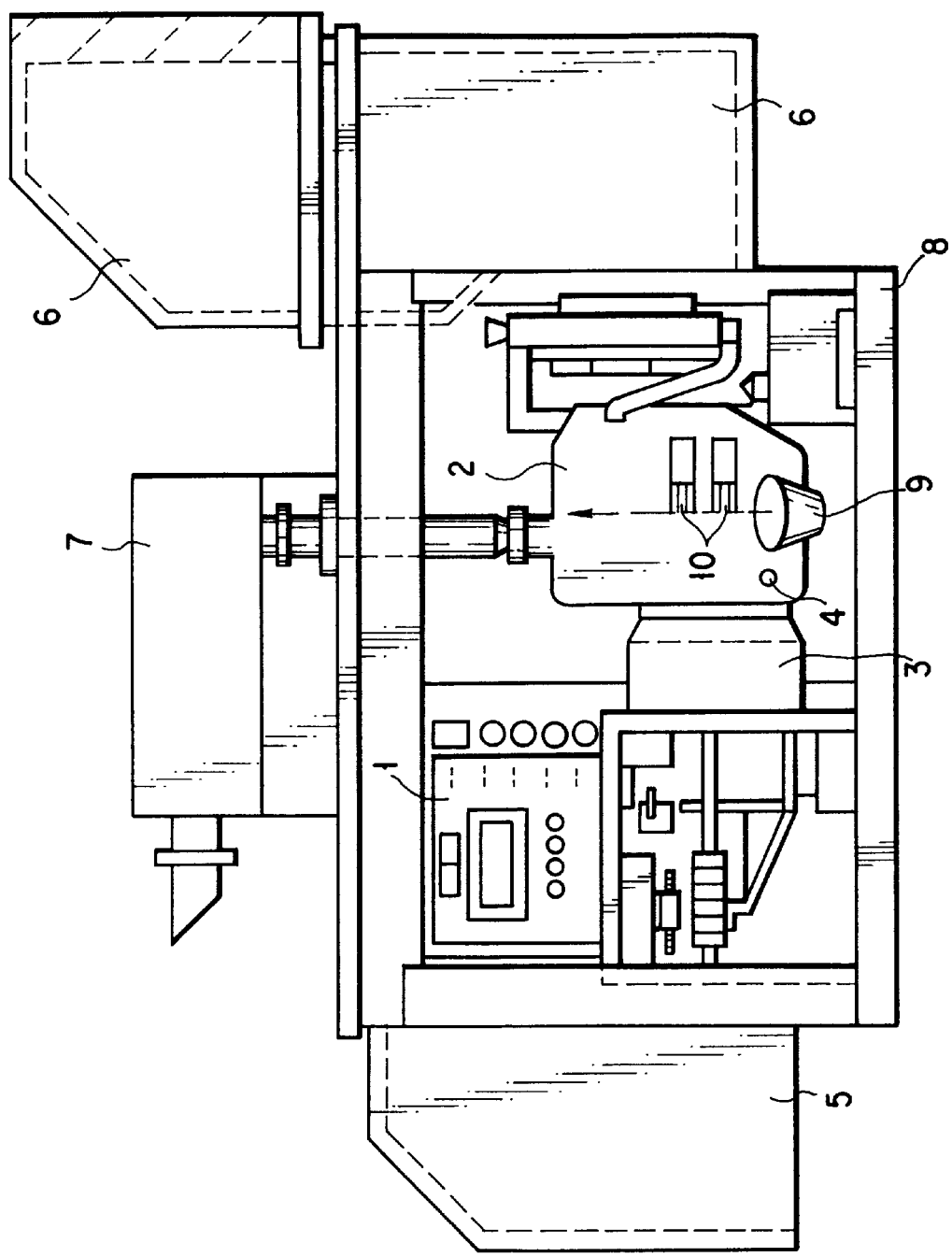
FIG. 12 is an outline showing the structure of a private power generator according to an eighth embodiment of the present invention.

FIG. 9 is a block diagram showing an outline structure of an active noise control apparatus according to the sixth embodiment of the present invention.

This embodiment shows a case in which the shortage of outputs occurs if the number of speakers is one since the aforementioned noise sources are large acoustic sources. To reduce the output load of one speaker, N speakers are dispersely arranged and the output shortage is compensated. In this case, N sets of two microphones are needed.

In the case of one additional sound source, the total acoustic power can be minimized when the acoustic emission power, which is radiated from the additional sound source radiated from the additional sound source as a result of mutual interference between the noise source and the additional sound source, is set to zero or minimized. Even when the plurality of additional sound sources are provided, the total acoustic power can be minimized if the emission power of the additional sound sources is set to be zero or minimized (more specifically, a sum of power emitted from one additional sound source when the additional sound sources sound one by one and power caused by mutual interference between the additional sound sources).

The following shows the calculation examples in which acoustic power reduction effect is confirmed when the plurality of additional sound sources are used in connection with wall surface transmitting sound: In this case, the wall surfaces can be obtained by a set of point sound sources.

First of all, as shown in FIGS. 10A to 10D, it is assumed that the additional sound sources are arranged in a matrix form to be opposite to the wall surfaces.

At this time, emission power of the additional sound sources can be obtained by the following equation (14):

$$W_Q = \frac{1}{2}Z_o\left[\sum_{is=1}^{Ms}\sum_{js=1}^{Ns}\sum_{is=1}^{Ms}\sum_{js=1}^{Ns}|Q_{isjs}\,Q_{i's'j's}|\mathrm{sinc}(kr_{iiji'j'})\cos(\theta_{ij}-\theta_{i'j'})\right] \quad (14)$$

Here, if all additional sound sources are controlled by the same phase and amplitude, the emission power of the additional sound sources can be obtained by the following equation (15):

$$Q_{isjs} = \theta_{i's'j's} = \theta_Q \quad (1 \leq i \leq Ms, 1 \leq j \leq Ns) \quad (15)$$

$$Q_{isjs} = Q_{i's'j's} = Q$$

wherein $\therefore W_Q = \frac{1}{2}Z_o\left[\sum_{is=1}^{Ms}\sum_{js=1}^{Ns}\sum_{is=1}^{Ms}\sum_{js=1}^{Ns}|Q \cdot Q|\mathrm{sinc}(kr_{isjsi's'j's})\right]$ Here, the mutual emission power between the additional sound source and the wall surface can be obtained by the following equation (16):

$$W_{Qq} + W_{qQ} = Z_o\left[\sum_{is=1}^{Ms}\sum_{js=1}^{Ns}\sum_{i=1}^{M}\sum_{j=1}^{N}|Q_{isjs}q_{ij}|\mathrm{sinc}(kd_{isjsij})\cos(\theta_{isjs}\theta_{ij})\right] \quad (16)$$

$$= Z_o\left[\sum_{is=1}^{Ms}\sum_{js=1}^{Ns}\sum_{i=1}^{M}\sum_{j=1}^{N}|Qq_{ij}|\mathrm{sinc}(kd_{isjsij})\cos(\theta_Q - \theta_q)\right]$$

wherein $d_{isjsij}$: distance from a sound source $(i_s, j_s)$ of additional sound sources to an element sound source $(i, j)$ of the wall surface, $d_{iji'j'}$: distance between the respective elements of the wall surface, $d_{isjsi'sj's}$: distance between the respective sound sources of the additional sound sources; and $q_{ij}$: intensity of the respective elements of the wall surface.

Moreover, the mutual emission power between the respective elements of the wall surfaces can be obtained by the following equation (17):

$$W_q = \frac{1}{2}Z_o\left[\sum_{i=1}^{M}\sum_{j=1}^{N}\sum_{i'=1}^{M}\sum_{j'=1}^{N}|q_{ij}q_{i'j'}|\mathrm{sinc}(kd_{iji'j'})\cos(\theta_{ij}-\theta_{i'j'})\right] \quad (17)$$

If all wall surfaces has the same phase and amplitude, the mutual emission power between the respective elements of the wall surface can be obtained by the following equation (18):

$$\theta_{ij} = \theta_{i'j'} = \theta \quad (18)$$

$$\therefore W_q = \frac{1}{2}Z_o\left(\sum_{i=1}^{M}\sum_{j=1}^{N}\sum_{i'=1}^{M}\sum_{j'=1}^{N}|q_{ij}q_{i'j'}|\mathrm{sinc}(kd_{iji'j'})\right)$$

Then, the entire acoustic power is $$W = W_Q + W_{Qq} + W_{qQ} + W_q. \quad (19)$$

$$d_{iji'j'} = d_{i+a} \times \sqrt{(i-i')^2 + (j-j')^2}$$

$$\therefore \frac{\partial W}{\partial |Q|} = \frac{1}{2}Z_o\left[2\sum_{is=1}^{Ms}\sum_{js=1}^{Ns}\sum_{is=1}^{Ms}\sum_{js=1}^{Ns}|Q|\mathrm{sinc}(kr_{isjsi's'j's}) + 2\sum_{is=1}^{Ms}\sum_{js=1}^{Ns}\sum_{is=1}^{Ms}\sum_{js=1}^{Ns}|q_{ij}|\mathrm{sinc}(kd_{isjsij})\cos(\theta_Q-\theta_q)\right] = 0$$

$$\frac{\partial W}{\partial \theta_Q} = \frac{1}{2}Z_o\left[-Z\sum\sum\sum\sum|Qq_{ij}|\mathrm{sinc}(kd_{isjsij})\sin(\theta_Q-\theta_q)\right]$$
$$= 0$$

From equation (19), the amplitude of the intensity of the additional sound source where the entire acoustic power is minimized, and its phase can be obtained by the following equation (20):

$$\theta_Q - \theta_q = \pi \qquad (20)$$

$$|Q| = \frac{\sum_{is=1}^{Ms}\sum_{js=1}^{Ns}\sum_{is=1}^{Ms}\sum_{js=1}^{Ns}|q_{ij}|\mathrm{sinc}(kd_{isjsij})}{\sum_{is=1}^{Ms}\sum_{js=1}^{Ns}\sum_{i's=1}^{Ms}\sum_{j's=1}^{Ns}\mathrm{sinc}(kr_{isjsi'sj's})}$$

Here, power of the additional sound sources can be obtained by the following equation (21):

$$W_Q + W_{qQ} = \frac{1}{2}Z_o\left[\sum_{is=1}^{Ms}\sum_{js=1}^{Ns}\sum_{is=1}^{Ms}\sum_{js=1}^{Ns}|Q|^2\mathrm{sinc}(kr_{isjsi'sj's}) + \sum_{is=1}^{Ms}\sum_{js=1}^{Ns}\sum_{i=1}^{M}\sum_{j=1}^{N}|Qq_{ij}|\mathrm{sinc}(kd_{isjsij})\cos(\theta_Q - \theta_q)\right] \qquad (21)$$

$$= \frac{1}{2}Z_o\left[\sum_{is=1}^{Ms}\sum_{js=1}^{Ns}\sum_{is=1}^{Ms}\sum_{js=1}^{Ns}\left(\frac{\sum_{is=1}^{Ms}\sum_{js=1}^{Ns}\sum_{i=1}^{M}\sum_{j=1}^{N}|q_{ij}|\mathrm{sinc}(kd_{isjsij})}{\sum_{is=1}^{Ms}\sum_{js=1}^{Ns}\sum_{i's=1}^{Ms}\sum_{j'S=1}^{NS}\mathrm{sinc}(kr_{isjsi'sj's})}\right)^2 \mathrm{sinc}(kr_{isjsi'sj's}) - \right.$$

$$\left. \sum_{is=1}^{Ms}\sum_{js=1}^{Ns}\sum_{i=1}^{M}\sum_{j=1}^{N}\left(\frac{\sum_{is=1}^{Ms}\sum_{js=1}^{Ns}\sum_{i=1}^{M}\sum_{j=1}^{N}|q_{ij}|\mathrm{sinc}(kd_{isjsij})}{\sum_{is=1}^{Ms}\sum_{js=1}^{Ns}\sum_{i's=1}^{Ms}\sum_{j's=1}^{Ns}\mathrm{sinc}(kr_{isjsi'sj's})}\right)|q_{ij}|\mathrm{sinc}(kd_{isjsij})\right]$$

$$= \frac{1}{2}Z_o\left[\frac{\left(\sum_{is=1}^{Ms}\sum_{js=1}^{Ns}\sum_{i=1}^{M}\sum_{j=1}^{N}|q_{ij}|\mathrm{sinc}(kd_{isjsij})\right)^2}{\sum_{is=1}^{Ms}\sum_{js=1}^{Ns}\sum_{is=1}^{Ms}\sum_{js=1}^{Ns}\mathrm{sinc}(kr_{isjsi'sj's})} - \frac{\left(\sum_{is=1}^{Ms}\sum_{js=1}^{Ns}\sum_{i=1}^{M}\sum_{j=1}^{N}|q_{ij}|\mathrm{sinc}(kd_{isjsij})\right)^2}{\sum_{is=1}^{Ms}\sum_{js=1}^{Ns}\sum_{is=1}^{Ms}\sum_{js=1}^{Ns}\mathrm{sinc}(kr_{isjsi'sj's})}\right]$$

$$= 0$$

Therefore, even if the plurality of additional sound sources are used, emission power $W_Q + W_{qQ}$ of additional sound sources becomes zero.

$$\therefore W_{ON} = W_Q W_{qQ} + W_{Qq} + W_q + W_{Qq} + W_q \quad W_{OFF} = W_q$$

The amount of reduction of the acoustic power at a control time can be expressed by the equation (22):

$$\eta = 10\log\frac{W_{ON}}{W_{OFF}} = 10\log\left(1 + \frac{W_{Qq}}{W_q}\right) \qquad (22)$$

$$= 10\log\left[1 + \frac{-\sum_{i=1}^{Ms}\sum_{j=1}^{Ns}\sum_{i=1}^{M}\sum_{j=1}^{N}|q_{ij}|\mathrm{sinc}(kd_{isjsij})}{\sum_{i=1}^{M}\sum_{j=1}^{N}\sum_{i=1}^{M}\sum_{j=1}^{N}|q_{ij}q_{i'j'}|\mathrm{sinc}(kd_{iji'j'})} \times \right.$$

$$\left. \frac{\sum_{is=1}^{Ms}\sum_{js=1}^{Ns}\sum_{i=1}^{M}\sum_{j=1}^{N}|q_{ij}|\mathrm{sinc}(kd_{isjsij})}{\sum_{is=1}^{Ms}\sum_{js=1}^{Ns}\sum_{is=1}^{Ms}\sum_{js=1}^{Ns}\mathrm{sinc}(kr_{isjsi'sj's})}\right]$$

Therefore, even when the plurality of additional sound sources are used, the entire acoustic power can be reduced if the emission power of the additional sound sources is controlled to be zero or minimized (more specifically, a sum of power emitted from one additional sound source when the additional sound sources sound one by one and power caused by mutual interference between the additional sound sources).

The system structure for realizing the above-mentioned point shown in FIG. 9, and has the same control system as shown in FIG. 3. In this case, as compared with the case of FIG. 3, attention should be paid to the point that power reduction of N additional sound sources must be simultaneously controlled when using N microphones and N. Unlike the case of FIG. 4, power cannot be reduced one by one in order.

Seventh Embodiment

FIG. 11 is a cross-sectional view showing an additionally provided device to the active noise control apparatus according to the seventh embodiment of the present invention.

In any method for reducing acoustic power radiated from the noise source in the aforementioned embodiments, the additional source is positioned on condition that the additional source should be made close to the noise source. However, there is a case in which sound emitted from the additional sound source cannot be made close to the noise source such as an engine due to a heating problem. A conduit 400 shown in FIG. 11 is provided to take measures against the heating problem. Sound emitted from the additional sound source 401 can be guided to a predetermined area of a noise source 402 to be emitted.

Even in the noise source having no heating problem, sound radiated from the additional sound source can be made close to the noise source by use of the conduit. As a result, noise elimination effect can be further improved.

Eighth Embodiment

Next, an eighth embodiment of the present invention will be explained. This embodiment relates to a private power generator to which the above-mentioned active noise control apparatus is applied.

More specifically, the private power generator of this embodiment relates to a private power generator for emergency. The private power generator comprises a controller 1, a generator 3, and an engine 2. The controller 1 performs a detection of a power cut due to a microcomputer, an automatic power feeding, and an automatic stopping power at a power recovery time. The style of the mounted engine is changed, thereby making it possible to generate an output ranging from a rated capacity of 16 kVA to 100 kVA. The private power generator further comprises a detecting section 4 for detecting a vibration signal of engine 2 or an engine rotation pulse signal, a control section for processing the signal obtained from the detecting section 4, a speaker for emitting the signal, serving as sound, generated by the control section to sound of the engine, a microphone for monitoring a level of the engine sound. Thereby, the engine sound can be actively eliminated.

More specifically, if a power cut occurs at an emergency time, the controller 1 receives a power cut confirmation command, and confirms a voltage. Then, power supply switching from the commercial power supply to a private generator is performed. Thereby, the engine 2 is started, and power feeding is performed through the generator. When the engine is started, the signal detecting section 4, which is provided on the surface of the engine, detects the vibration of the engine correlated with the engine sound. The detected vibration is input to the controller 1, and sound whose phase is opposite to the engine sound is generated so as to be emitted from the speaker to the engine. Then, the controller 1 controls acoustic intensity, which is detected by two microphones provided on an axis perpendicular to the vibration surface of the speaker, to be zero or minimized. When acoustic intensity is zero or minimized, engine emission power becomes minimum, and noise around the engine is reduced.

The above-explained apparatus is called a low noise type private generator for about 85 dB(A) within 1 m around the engine (floor level of 1.2 m).

There is an extremely low noise type apparatus for 75 dB(A) has capacity about 1.5 times as large as the low noise type apparatus for 85 dB(A). In this apparatus, to reduce noise having a low frequency as a main component by 10 dB, a sound absorbing process having a small sound elimination effect in the low frequency is provided, so that the volume is enlarged, and the area of a soundproof cover is increased. Therefore, if the active noise control apparatus of the present invention is mounted on the low noise type private generator for 85 dB(A), the reduction of about 10 dB can be realized without changing the structure, and this can be commercialized as an extremely low noise type apparatus for 75 dB(A) having the same capacity as the low noise type apparatus for 85 dB(A).

Ninth Embodiment

Next, a ninth embodiment of the present invention will be explained. This embodiment relates to a transformer to which the above-mentioned active noise control apparatus is applied.

The transformer of this embodiment comprises an iron core, a coil, insulating oil, and a tank for covering these members. By changing the size of the iron core, its weight, the number of wires of the coil, and density of magnetic flux, the capacity can be enlarged. The transformer of this embodiment further comprises a soundproof cover, and a soundproof tank to satisfy a predetermined noise value at a delivery time. Moreover, the transformer of this embodiment comprises an active noise control apparatus for eliminating low frequency electromagnetic sound, which is not easily reduced by the soundproof cover and the soundproof tank, and which is generated by magnetostriction vibration.

As a three-phase transformer, a three-leg core is generally used. If the transformer having large capacity to be transported by a freight car is used, a five-leg core is used to be contained within the limited height.

Regarding the transportation of the single-phase transformer, there is a strict limitation in Japan. For example, This is limited to a special three-phase transformer comprising three single-phase transformers, and a 500 kV transformer of large-size and capacity. Due to this, a two-leg core is known as a single-phase transformer core. Actually, the three-leg core, or four-leg or five-leg core is used in the case of the large capacity. In this case, since an amount of leak magnetic flux is increased, a number of cooling oil paths are provided to prevent local overheating, thereby forcible cooling is executed.

The coil is wound around the core, and the capacity can be changed depending on the number of winding. In order to prevent stress being applied to oil around the core, an insulating structure is provided on the wire end of a disk wire, a layer end portion of a cylindrical wire, or a portion where an electrical field easily concentrates such as a connecting portion of a lead pulled out of the coil. Then, insulating oil fills the portion around the insulating structure.

The cause of noise, which is generated from the transformer having the structure in these members are covered with the tank made of a steel plate, can be generally classified to the following three points:

(1) Electromagnetic mechanical force between wires;
(2) Magnetic absorbing force between the seam of the cores or between the respective layers; and
(3) Magnetrostriction vibration of silicon steel plate (core).

The electromagnetic mechanical force and the magnetic absorbing force can be largely reduced by sufficiently fastening the wire and the core. Therefore, noise caused by magnetostriction vibration is generally regarded as a transformer noise.

However, in the case of point (3), the noise generation mechanism is considerably complicated, and noise is changed by influence of magnetrostriction vibration of the silicon steel plate to be used, the density of magnetic flux, the size of the core, the weight. For example, in the case of the fixed core, the more the density of magnetic flux increases, the more the amount of magnetirostriction increases, and noise is increased. For example, noise is increased by 2 to 3 dB with increase of 1000 gauss. Since the magnetrostriction vibration obtains its maximum value every half cycle of magnetization, a higher harmonic wave where double excitation frequency is used as a basic frequency appears.

The vibration of such core is transmitted to the tank side surface through the following passages:

(1) core→cross bar of lower portion→bottom plate of tank→side plate;
(2) core→insulating oil→side surface of tank.

Conventionally, the following measures were taken:

(1) The magnetrostriction vibration of the core is reduced. As a specific method, there are reduction of the density of magnetic flux, selection of steel plate material, improvement of fastening mechanism.
(2) The contents of the transformer is supported to the bottom portion of the tank to prevent the transformer from being vibrated.
(3) An accumulator (bag filled with air) is provided in an inner wall surface of the tank so as to prevent the transmission of vibration due to liquid.
(4) The wall surface material of the tank having a large lost coefficient is used.

If the above-mentioned measures do not satisfy the predetermined noise value at the delivery time, measures to cover the main body of the tank of the transformer is further considered.

For example, in the transformer having large capacity of 100 to 300 MVA, the following kinds of structure are used in accordance with the predetermined noise value.

(1) Noise Value of 70 to 80 dB

The side wall of the main body of the transformer is covered with the soundproof cover, and there is used a low noise unit cooler in which the number of rotations of fan is reduced.

(2) Noise Value of 60 to 70 dB

The main body of the transformer is covered with a soundproof tank made of an iron plate. As a cooler, there is used a low noise unit cooler in which the number of rotations of fan is reduced, or a low noise unit cooler with a sound absorbing duct.

(3) Noise Value of 55 to 65 dB

The main body of the transformer is covered with the soundproof tank made of a concrete panel. As a cooler, there is used a low noise unit cooler with a sound absorbing duct, or a radiating bank.

(4) Noise Value of 50 to 60 dB

The main body of the transformer is placed in a concrete soundproof housing. As a cooling system, a oil feed self-cooling system is generally used, and the radiating bank is placed at the outside of the housing.

However, if such noise cannot be reduced in the core portion of the noise generating source, a large scale of work and a large amount of cost are needed to reduce noise. For example, if the tank is covered with concrete, noise can be reduced. However, this increases not only cost but also weight, and it is difficult to say that this is a suitable method in view of the mounting work. In the present state, there is no other way than the use of concrete. The reason lines in the point that the main component of the noise of the transformer is a low frequency area, and the transmission lost coefficient of noise is small. Since surface density cannot be sufficiently obtained from the steel plate, a sound isolation effect cannot be expected. To solve this problem, the following will describe a method for reducing noise of the transformer by use of the active noise control technique in which the noise reduction effect is improved as the frequency is lower.

In this case, the measures against noise in the following two case will be considered:

(1) One is electromagnetic noise, which is caused by magnetostriction vibration of the core. Electromagnetic noise is propagated to the tank side wall of the transformer through the insulating oil, and transmitted to the side wall surface to be emitted to the three-dimensional space (FIG. 14).

Figure 15:
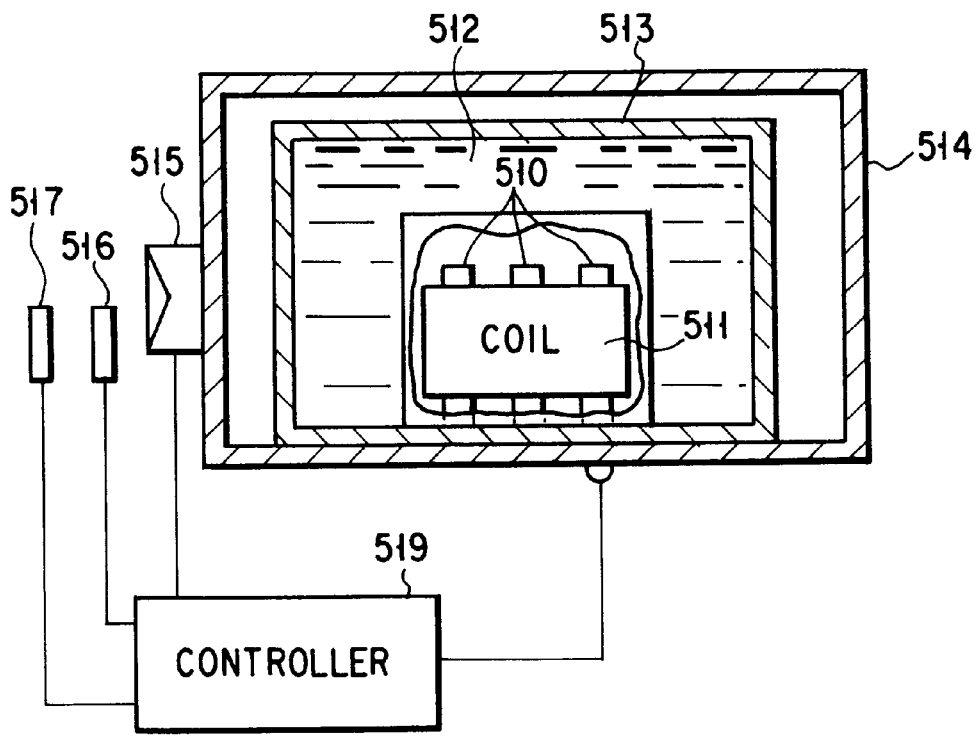
FIG. 15 is a block diagram showing a second structure of the active noise control apparatus applied to a transformer according to the ninth embodiment of the present invention.

(2) The other is electromagnetic noise, which is caused by magnetostriction vibration of the core. In a case where the entire the tank of the transformer is covered with the soundproof, electromagnetic noise is transmitted through the tank side wall surface and soundproof cover to be emitted to the three-dimensional space (FIG. 15).

Figure 14:
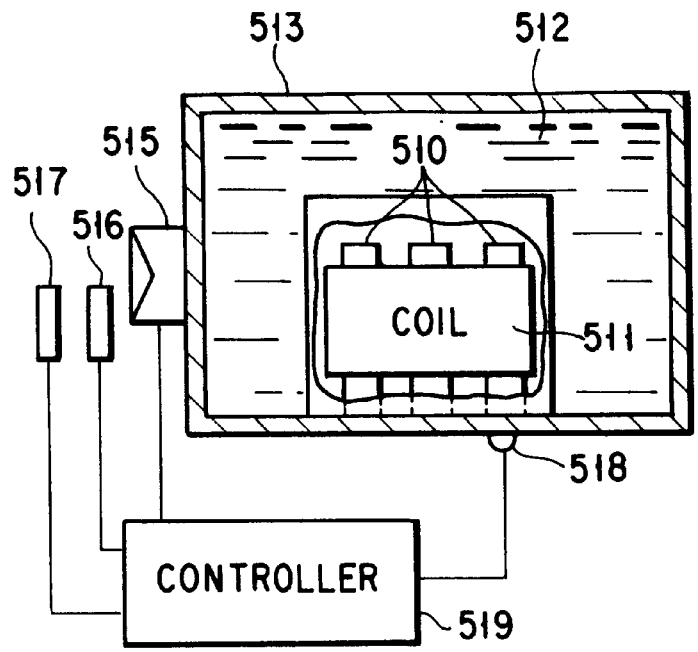
FIG. 14 is a block diagram showing a first structure of the active noise control apparatus applied to a transformer according to a ninth embodiment of the present invention.

FIG. 14 is the block diagram showing a first structure of the transformer having the active noise control apparatus of the embodiment of the present invention. As shown in this figure, a core 510, a coil 511, and insulating oil 512 are contained in a tank (main body) 513.

An active speaker 515 is attached to the wall surface of the tank 513, and its output is controlled by a controller 519. Two microphones 516 and 517 are arranged on the central axis of the vibration surface of the active speaker 515 to be spaced with each other. Then, a sound pressure signal and a particle velocity signal, which are measured by the microphones 516 and 127, are introduced to the controller 519.

The controller 519 has a calculation section, which calculates average sound pressure between the microphones between the sound pressure signals of the microphones 516 and 517, and calculates acoustic intensity, which a time average of the particle velocity.

A detection section 518 for obtaining a reference signal, which is correlated with generating noise, is attached onto the tank 513 as a noise source. The reference signal obtained by the detection section 518 is sent to the controller 519.

On one hand, the reference signal is introduced to an FIR filter 40 for a control coefficient. At this time, the reference signal is multiplied by a control coefficient to serve as an input signal for the speaker 515. On the other hand, the reference signal is further divided to two to be introduced to an FIR filter for an intensity coefficient obtained by the microphones 516 and 517 and sent from the speaker 515. Then, a sum of products of each reference signal and the original signal is calculated, and the result is sent to a calculation section for a control coefficient (not shown).

The calculation section renews the control coefficient (filter coefficient) of the FIR filter for a control coefficient such that acoustic intensity emitted from the speaker by filter-XLMS algorithm becomes near zero.

Figure 16:
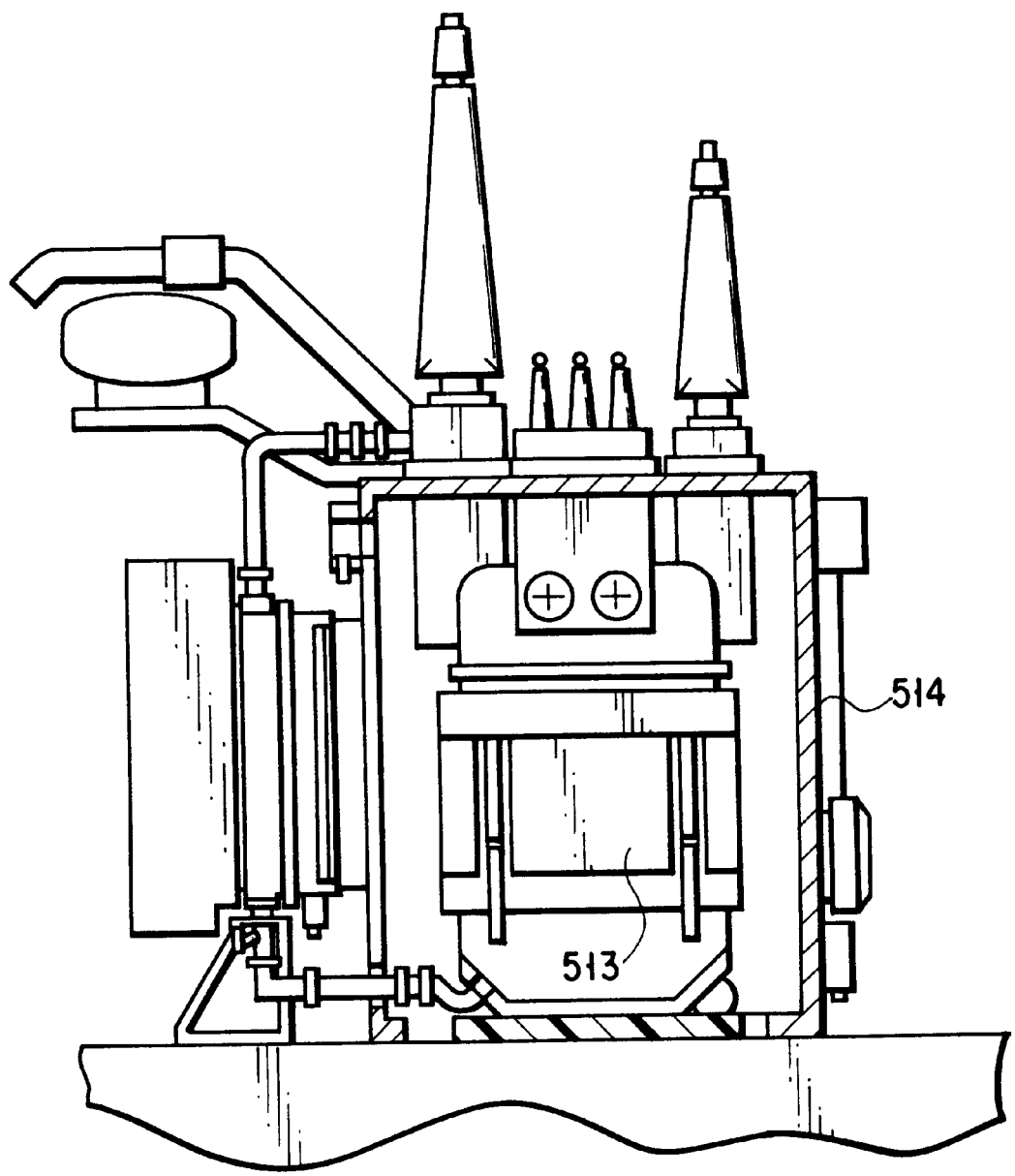
FIG. 16 is a partial cross-sectional view showing the structure of the transformer according to the ninth embodiment of the present invention.

FIG. 15 is the block diagram showing a second structure of the transformer having the active noise control apparatus of the embodiment of the present invention. The second structure has the soundproof cover (or soundproof tank) 514 covering the entire tank 513. The active speaker 515 is attached to the wall surface of the soundproof cover 514. FIG. 16 is a partially cross-sectional view showing the specific structure of the transformer of the second structure.

As an input signal for an active control, a voltage signal for exciting the coil or a current signal is used in either case (1) and (2). In case (1), to eliminate noise caused by vibration of the tank side wall surface, the active speaker (additional sound source) is provided close to the vibration surface (wall surface). In case (2), to eliminate noise caused by vibration of the soundproof cover, the active speaker (additional sound source) is provided close to the vibration surface (wall surface). Moreover, as mentioned above, by two microphones, which are arranged on the axis of the vibration surface of the active speaker to be spaced from each other, acoustic intensity of the active speaker is measured. Then, the adaption control is performed such that acoustic intensity is minimized. Thereby, acoustic emission power transmitted from the vibration surface can be reduced, and noise expanding in the three-dimensional space can be reduced.

In this case, if the vibration surface has a mode, at least one active speaker is arranged at the position of the loops of the mode. As a result, if acoustic intensity from each speaker can be reduced, all loops can be reduced, so that wall surface transmission acoustic power having the mode can be reduced.

As mentioned above, according to the present invention, there can reduce noise, which is generated by the apparatus placed in the three-dimensional space, without having the complicated structure.

Additional advantages and modifications will readily occurs to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An active noise control apparatus for controlling a noise caused by a noise source, comprising:

an additional sound source provided close to the noise source;

acoustic power measuring means, provided adjacent to the additional sound source for measuring acoustic power radiated front the additional sound source as a result of mutual interference between the noise source and the additional sound source; and controlling means for controlling an output of the additional sound source such that the acoustic power radiated from the additional sound source and measured by the measuring means is minimized.

2. The apparatus according to claim 1, wherein the acoustic power measuring means comprises acoustic intensity measuring means for measuring acoustic intensity radiated from the additional sound source as a result of mutual interference between the noise source and the additional sound source.

3. The apparatus according to claim 1, wherein the controlling means sequentially provides an input signal to the additional sound source such that acoustic power measured by the acoustic power measuring means is set to be equal to zero.

4. The apparatus according to claim 3, wherein the controlling means comprises a filter and calculation section.

5. An active noise control apparatus for controlling noise caused by a noise source, comprising:

an additional sound source located adjacent to the noise source;

acoustic intensity measuring means having at least two microphones, provided on same side on a central axis of a vibration surface of the additional sound source spaced from each other, for measuring, an acoustic intensity radiated from the additional sound source as a result of mutual interference between the noise source and the additional sound source; and controlling means for controlling an output of the additional sound source such that the acoustic power radiated from the additional sound source and measured by the measuring means is minimized.

6. The apparatus according to claim 5, wherein the controlling means sequentially provides an input signal to the N sound sources such that acoustic power measured by the acoustic power measuring means is set to be equal to zero.

7. The apparatus according to claim 6, the controlling means comprises a single adaptation control means for controlling each of the N sound sources, and the adaptation control means controls the sound sources one by such that acoustic power of N loops of same phase surfaces of the noise source are reduced one by one.

8. An active noise control method for controlling a noise by driving an additional sound source provided close to a noise source to cause sound interference between the noise source and the additional sound source, comprising the steps of:

measuring an acoustic power radiated from the additional sound source as a result of mutual interference between the noise source and the additional sound source in a vicinity of the additional sound source; and controlling an output of the additional sound source such that the acoustic power radiated from the additional sound source and measured by the measuring means is minimized.

9. A stand-alone power generator having an active noise control apparatus for controlling noise from an engine driving a generator, comprising:

an additional sound source located adjacent to the engine;

acoustic power measuring means, provided adjacent to the additional sound source, for measuring an acoustic power radiated from the additional sound source as a result of mutual interference between sound of the engine and sound of the additional sound source; and controlling means for controlling an output of the additional sound source such that the acoustic power measured by the measuring means is minimized.

10. A transformer in an active noise control apparatus for controlling noise from a tank containing a core, a coil, and insulating oil, comprising:

a sound source located adjacent to the tank;

acoustic power measuring means for measuring an acoustic power radiated from the sound source as a result of mutual interference between noise from the tank and sound of the sound source; and controlling means for controlling an output of the sound source such that the acoustic power measured by the measuring means is minimized.

11. The apparatus according to claim 10, further comprising soundproof means covering a tank having the core, the coil, and the insulating oil.

* * * * *